US008796420B2

(12) United States Patent
Martin, Jr. et al.

(10) Patent No.: US 8,796,420 B2
(45) Date of Patent: *Aug. 5, 2014

(54) NON-NATURAL MIC PROTEINS

(75) Inventors: David W. Martin, Jr., Mill Valley, CA (US); Steven R. Williams, San Francisco, CA (US)

(73) Assignee: AvidBiotics Corp., South San Francisco, CA (US)

( * ) Notice: Subject to any disclaimer, the term of this patent is extended or adjusted under 35 U.S.C. 154(b) by 281 days.

This patent is subject to a terminal disclaimer.

(21) Appl. No.: 13/176,601

(22) Filed: Jul. 5, 2011

(65) Prior Publication Data
US 2011/0311561 A1    Dec. 22, 2011

Related U.S. Application Data

(63) Continuation-in-part of application No. 12/982,827, filed on Dec. 30, 2010.

(60) Provisional application No. 61/291,749, filed on Dec. 31, 2009.

(51) Int. Cl.
*A61K 38/16* (2006.01)
*C07K 16/00* (2006.01)
*A01N 63/00* (2006.01)
*C07K 19/00* (2006.01)
*C12N 5/0783* (2010.01)

(52) U.S. Cl.
USPC .................. 530/345; 530/350; 530/387.1

(58) Field of Classification Search
None
See application file for complete search history.

(56) References Cited

U.S. PATENT DOCUMENTS

| 7,771,718 B2 | 8/2010 | Spies et al. |
| 2009/0226466 A1 | 9/2009 | Fong et al. |
| 2011/0183893 A1 | 7/2011 | Martin, Jr. et al. |

FOREIGN PATENT DOCUMENTS

| WO | WO00/06605 | 2/2000 |
| WO | WO2005/052004 | 6/2005 |
| WO | WO2005/061547 | 7/2005 |
| WO | WO2006/024367 A2 | 3/2006 |
| WO | WO2007/068354 | 6/2007 |
| WO | WO 2007/097812 | 8/2007 |
| WO | WO2008/058728 | 5/2008 |

OTHER PUBLICATIONS

Bahram, S., et al., "A Second Lineage of Mammalian MHC Class I Genes," PNAS 91:6259-6263 (1994).
Bahram, S., et al., "Nucleotide Sequence of the Human MHC Class I MICA Gene," Immunogenetics 44:80-81 (1996).
Bahram, S., et al., "Nucleotide Sequence of Human MHC Class I MICB cDNA," Immunogenetics 43:230-233 (1996).
Bargou, R., et al., "Tumor Regression in Cancer Patient by Very Low Doses of a T Cell Engaging Antibody," Science 321:974 (2008).
Bauer, S., et al., "Activation of NK Cells and T Cells by NKG2D, A Receptor for Stress-Inducible MICA," Science 285:727-730 (1999).
Busche, A., et al., "NK Cell Mediated Rejection of Experimental Human Lung Cancer by Genetic Over Expression of MHC Class I Chain-Related Gene A," Human Gene Therapy 17:135-146 (2006).
Chang, C., et al., "NK Cell Activating Ligands on Human Malignant Cells: Molecular and Functional Defects and Potential Clinical Relevance," Seminars in Cancer Biology 16:383-392 (2006).
Coudert, J., et al., "The Role of the NKG2D Receptor for Tumor Immunity," Seminars in Cancer Biology 16:333-343 (2006).
Diefenbach, A., et al., "Strategies for Target Cell Recognition by Natural Killer Cells," Immunol. Reviews 181:170-184 (2001).
Donda, A., et al., "In Vivo Targeting of an Anti-Tumor Antibody Coupled to Antigenic MHC Class I Complexes Induces Specific Growth Inhibition and Regression of Established Syngeneic Tumor Grafts," Cancer Immun. 14:3-11 (2003).
Friese, M., et al., "MICA/NKG2D—Mediated Immunogene Therapy of Experimental Gliomas," Cancer Research 63:8996-9006 (2003).
Fuertes, M., et al., "Intracellular Retention of the NKG2D Ligand MHC Class I Chain Related Gene A in Human Melanomas Confers Immune Privilege and Prevents NK Cell-Mediated Cytoxicity," J. Immunol. 180:4606-4614 (2008).
Gasser, S., et al., "The DNA Damage Response, Immunity and Cancer," Seminars in Cancer Biology 16:344-347 (2006).
Bahram, S., et al., GenBank Report Accession No. AAA21718, MHC class I-related protein (*Homo sapiens*), submitted 1994.
Germain, C., et al., "MHC Class I-Related Chain a Conjugated to Antitumor Antibodies Can Sensitize Tumor Cells to Specific Lysis by Natural Killer Cells," Clinical Cancer Res. 11(20):7516-7522 (2005).
Groh, V., et al., "Co-Stimulation of CD8+ αβT-Cells by NKG2D Via Engagement by MIC Induced on Virus-Infected cells," Nat. Immunol. 2:255-260 (2001).
Guo, H., et al., "Diversity-Generating Retroelement Homing Regenerates Target Sequences for Repeated Rounds of Codon Rewriting and Protein Diversification," Molecular Cell 31:813-823 (2008).
Holmes, M.A., et al., "Structural Studies of Allelic Diversity of the MHC Class I Homolog MICB, a Stress-Inducible Ligand for the Activating Immunoreceptor NKG2D," J. Immunol. 169:1395-1400 (2001).
Jager, M., et al., "The Trifunctional Antibodyertumaxomad Destroys Tumor Cells That Express Low Levels of Human Epidermal Growth Factor Receptor 2," Cancer Res. 69(10):4270-4276 (2009).

(Continued)

*Primary Examiner* — Gerald R Ewoldt
*Assistant Examiner* — Marianne Dibrino
(74) *Attorney, Agent, or Firm* — Sughrue Mion, PLLC

(57) ABSTRACT

This invention describes soluble, monovalent, non-natural protein molecules that can activate NK cells and certain T-cells to attack specific cellular target cells by attaching the NKG2D-binding portions of monovalent MICA or MICB protein, i.e. their α1-α2 platform domain, to the intended target cell specifically. The α1-α2 domain is contiguous with a heterologous α3 domain that has been genetically modified to bind directly or indirectly to the extracellular aspect of the target cell, thereby serving as the targeting domain. The genetic modification to create a non-natural and non-terminal targeting motif within the α3 domain can include a portion of an antibody, another protein molecule or portion thereof, a peptide, or a non-natural, modified α3 domain of a MIC protein.

27 Claims, 13 Drawing Sheets

(56) References Cited

OTHER PUBLICATIONS

Figure 1:
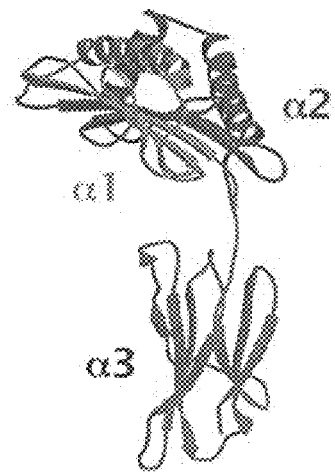

Koide, A., et al., "High Affinity Single-Domain Binding Proteins With a Binary-Code Interface," PNAS 104(16):6632-6637 (2007).

Lev, A., et al., "Recruitment of CTL Activity by Tumor-Specific Antibody-Mediated Targeting of Single-Chain Class IMHC-Peptide Complexes," J. Immunol. 169:2988-2996 (2002).

Lev, A., et al., "Tumor Specific Ab-Mediated Targeting of MHC-Peptide Complexes Induces Regression of Human Tumor Xenografts in Vivo," Proc. Natl. Acad. Sci. USA 14:3-11 (2004).

Li, P., et al., "Crystal Structure of the MHC Class I Homolog MICA, A γσ T Cell Ligand," Immunity 10:577-584 (1999).

Ogg, G.S., et al., "Sensitization of Tumour Cells tTo Lysis by Virus-Specific CTL Using Antibody-Targeted MHC Class I/Peptide Complexes," Br. J. Cancer 82:1058-1062 (2000).

Robert, B., et al., "Antibody-Conjugated MHC Class I Tetramers Can Target Tumor Cells for Specific Lysis by T Lymphocytes," Eur. J. Immunol. 30:3165-3170 (2000).

Robert, B., et al., "Redirecting Anti-Viral CTL Against Cancer Cells by Surface Targeting of Monomeric MHC Class I-Viral Peptide Coupled to Antibody Fragments," Cancer Immunol. 1:2 (2001).

Steinle, A., et al., "Interactions of Human NKG2D with Its Ligands MICA, MICB and Homologs of the Mouse RAE-1 Protein Family," Immunogenetics 53:279-287 (2001).

Stephens, H.A., "MICA and MICB Genes: Can the Enigma of Their Polymorphism Be Resolved?" Trends Immunol. 22:378-85 (2001).

Stern-Ginossar, et al., "Host Immune System Gene Targeting by Viral miRNA," Science 317:376-381 (2007).

Stern-Ginossar, et al. "Human microRNAs Regulate Stress-Induced Immune Responses Mediated by the Receptor NKG2D," Nature Immunol. 9:1065-1073 (2008).

Suck, G., et al., "Novel Approaches Using Natural Killer Cells in Cancer Therapy," Seminars in Cancer Biology 16:412-418 (2006).

Touze T., et al., "Self-Association of EPEC Intimin Mediated by the Beta-Barrel-Containing Anchor Domain: A Role in Clustering of the Tir Receptor," Mol. Microbiol. 51:73-87 (2004).

Uherek, C., et al., "Retargeting of Natural Killer-Cell Cytolytic Activity to ErbB2—Expressing Cancer Cells Results in Efficient and Selective Tumor Cell Destruction," Blood 10:1265-1273 (2002).

Weis, W.I., et al., "The C-type Lectin Superfamily of the Immune System," Immunol. Rev. 163:19-34 (1998).

Wentzel, A., et al., "Display of Passenger Proteins on the Surface of *Escherichia coli* K-12 by the Enterohemorrhagic *E. coli* Intimin EaeA," J. Bacteriol. 183:7273-84 (2001).

Zwirner, N., et al, "Differential Surface Expression of MICA by Endothelial Cells, Fibroblasts, Keratinocytes and Monocytes," Human Immunol. 60:323-330 (1999).

Martin, D.W., "Targeted Soluble MICA Molecules to Recruit Innate Immunity Cells to Kill Specific," Project No. 1R43AI088979-01, Internet, Mar. 15, 2010, XP002662442, Retrieved from the Internet: URL:http://projectreporter.nih.gov/project_info_description.cfm?aid=7907360&icde=0[retrieved on Oct. 27, 2011].

Zwirner, N., et al., "Immunobiology of The Human MHC Class I Chain-Related Gene A (MICA): From Transplantation Immunology to Tumor Immune Escape," Immunologia 25(1):25-38 (2006).

Gong, Wei-Juan, et al., "[Effects of recombinant soluable MICA protein on the biologic activities of NK cells]," Xi Bao Yu Fen Zi Mian Yi Xue Za Zhi = Chinese Journal of Cellular and Molecular Immunology Oct. 2009 LNKD-PUBMED: 19811738, vol. 25, No. 10, Oct. 2009, pp. 903-906, abstract.

Marten, A.,, et al., "Inhibition of Cytotoxic Gamma/Delta T Cells by Pancreatic Carcinoma Patients' Derived Soluble MIC+ Serum Could Be Restored by Capturing Soluble MIC With Antibodies," Gastroenterology 128(4) Suppl. 2, (Apr. 1, 2005), p. A532, T1699.

Robinson, J., et al., "MICA Sequences 2000," Immunogenetics 53(2):150-169 (2001).

Li, P., et al., "Complex Structure of the Activating Immunoreceptor NKG2D and Its MHC Class I-Like Ligand MICA," Nat. Immunol. 2(5):443-451 (2001).

Groh, V. et al., "Tumour-derived Soluble MIC Ligands Impair Expression of NKG2D and T-Cell Activation," Nature 419:734-8 (2002).

Vetter, C. et al., "Loss of Nonclassical MHC Molecules MIC-A/B Expression During Progression of Uveal Melanoma," British Journal of Cancer 91:1495-9 (2004).

Weiner, L. et al., "Targeted Therapy" Fox Chace Cancer Center 2006 Scientific Report, Internet at www.fccc.edu/docs/sci_report/Weiner.pdf.

```
SEQ. ID. NO. 1    MICA
      1 EPHSLRYNLT VLSWDGSVQS GFLTEVHLDG QPFLRCDRQK CRAKPQGQWA EDVLGNKTWD
     61 RETRDLTGNG KDLRMTLAHI KDQKEGLHSL QEIRVCEIHE DNSTRSSQHF YYDGELFLSQ
    121 NLETEEWTMP QSSRAQTLAM NVRNFLKEDA MKTKTLYHAM HADCLQELRR YLKSGVVLRR
    181 TVPPMVNVTR SEASEGNITV TCRASGFYPW NITLSWRQDG VSLSHDTQQW GDVLPDGNGT
    241 YQTWVATRIC QGEEQRFTCY MEHSGNHSTH PVPS

SEQ. ID. NO. 2    MICA
      1 EPHSLRYNLT VLSWDGSVQS GFLAEVHLDG QPFLRCDRQK CRAKPQGQWA EDVLGNKTWD
     61 RETRDLTGNG KDLRMTLAHI KDQKEGLHSL QEIRVCEIHE DNSTRSSQHF YYDGELFLSQ
    121 NLETEEWTMP QSSRAQTLAM NIRNFLKEDA MKTKTHYHAM HADCLQELRR YLKSGVVLRR
    181 TVPPMVNVTR SEASEGNITV TCRASGFYPW NITLSWRQDG VSLSHDTQQW GDVLPDGNGT
    241 YQTWVATRIC QGEEQRFTCY MEHSGNHSTH PVPS

SEQ. ID. NO. 3    MICA
      1 EPHSLPYNLT VLSWDGSVQS GFLAEVHLDG QPFLRYDRQK CRAKPQGQWA EDVLGNKTWD
     61 RETRDLTGNG KDLRMTLAHI KDQKEGLHSL QEIRVCEIHE DNSTRSSQHF YYDGELFLSQ
    121 NLETEEWTMP QSSRAQTLAM NVRNFLKEDA MKTKTHYHAM HADCLQELRR YLKSGVVLRR
    181 TVPPMVNVTR SEASEGNITV TCRASGFYPW NITLSWRQDG VSLSHDTQQW GDVLPDGNGT
    241 YQTWVATRIC QGEEQRFTCY MEHSGNHSTH PVPS

SEQ. ID. NO. 4    MICA
      1 EPHSLRYNLT VLSWDGSVQS GFLAEVHLDG QPFLRYDRQK CRAKPQGQWA EDVLGNKTWD
     61 RETRDLTGNG KDLRMTLAHI KDQKEGLHSL QEIRVCEIHE DNSTRSSQHF YYDGELFLSQ
    121 NLETEEWTVP QSSRAQTLAM NVRNFLKEDA MKTKTHYHAM HADCLQELRR YLESGVVLRR
    181 TVPPMVNVTR SEASEGNITV TCRASSFYPR NIILTWRQDG VSLSHDTQQW GDVLPDGNGT
    241 YQTWVATRIC QGEEQRFTCY MEHSGNHSTH PVPS

SEQ. ID. NO. 5    MICA
      1 EPHSLRYNLT VLSWDGSVQS GFLTEVHLDG QPFLRCDRQK CRAKPQGQWA EDVLGNKTWD
     61 RETRDLTGNG KDLRMTLAHI KDQKEGLHSL QEIRVCEIHE DNSTRSSQHF YYDGELFLSQ
    121 NLETEEWTMP QSSRAQTLAM NVRNFLKEDA MKTKTHYHAM HADCLQELRR YLKSGVVLRR
    181 TVPPMVNVTR SEASEGNITV TCRASGFYPW NITLSWRQDG VSLSHDTQQW GDVLPDGNGT
    241 YQTWVATRIC QGEEQRFTCY MEHSGNHSTH PVPS

SEQ. ID. NO. 6    MICA
      1 EPHSLRYNLT VLSWDGSVQS GFLAEVHLDG QPFLRCDRQK CRAKPQGQWA EDVLGNKTWD
     61 RETRDLTGNG KDLRMTLAHI KDQKEGLHSL QEIRVCEIHE DNSTRSSQHF YYDGELFLSQ
    121 NLETEEWTMP QSSRAQTLAM NVRNFLKEDA MKTKTHYHAM HADCLQELRR YLKSGVVLRR
    181 TVPPMVNVTR SEASEGNITV TCRASGFYPW NITLSWRQDG VSLSHDTQQW GDVLPDGNGT
    241 YQTWVATRIC QGEEQRFTCY MEHSGNHSTH PVPS

SEQ. ID. NO. 7    MICB
      1 PHSLRYNLMV LSQDGSVQSG FLAEGHLDGQ PFLRYDRQKR RAKPQGQWAE DVLGAKTWDT
     61 ETEDLTENGQ DLRRTLTHIK DQKGGLHSLQ EIRVCEIHED SSTRGSRHFY YDGELFLSQN
    121 LETQESTVPQ SSRAQTLAMN VTNFWKEDAM KTKTHYRAMQ ADCLQKLQLP PMVNVICSEV
    181 SEGNITVTCR ASSFYPRNIT LTWRQDGVSL SHNTQQWGDV LPDGNGTYQT WVATRIRQGE
    241 EQRFTCYMEH SGNHGTHPVP SGKALVLQSQ RTDFPYVSAA MPCFVIIIIL CVPCCKKKTS
    301 AAEGP
```

Figure 7A

```
SEQ. ID. NO. 8     MICB
    1 PHSLRYNLMV LSQDGSVQSG FLAEGHLDGQ PFLRYDRQKR RAKPQGQWAE DVLGAETWDT
   61 ETEDLTENGQ DLRRTLTHIK DQKGGLHSLQ EIRVCEMHED SSTRGSRHFY YNGELFLSQN
  121 LETQESTVPQ SSRAQTLAMN VTNFWKEDAM KTKTHYRAMQ ADCLQKLQRY LKSGVAIRRT
  181 VPPMVNVTCS EVSEGNITVT CRASSFYPRN ITLTWRQDGV SLSHNTQQWG DVLPDGNGTY
  241 QTWVATRIRQ GEEQRFTCYM EHSGNHGTHP VPSGKALVLQ SQRTDFPYVS AAMPCFVIII
  301 ILCVPCCKKK TSAAEGP

SEQ. ID. NO. 9     MICB
    1 PHSLRYNLMV LSQDGSVQSG FLAEGHLDGQ PFLRYDRQKR RAKPQGQWAE DVLGAKTWDT
   61 ETEDLTENGQ DLRRTLTHIK DQKGGLHSLQ EIRVCEIHED SSTRGSRHFY YDGELFLSQN
  121 LETQESTVPQ SSRAQTLAMN VTNFWKEDAM KTKTHYRAMQ ADCLQKLQRY LKSGVAIRRT
  181 VPPMVNVICS EVSEGNITVT CRASSFYPRN ITLTWRQDGV SLSHNTQQWG DVLPDGNGTY
  241 QTWVATRIRQ GEEQRFTCYM EHSGNHGTHP VPSGKALVLQ SQRTDFPYVS AAMPCFVIII
  301 ILCVPCCKKK TSAAEGP

SEQ. ID. NO. 10    MICB
    1 PHSLRYNLMV LSQDGSVQSG FLAEGHLDGQ PFLRYDRQKR RAKPQGQWAE NVLGAKTWDT
   61 ETEDLTENGQ DLRRTLTHIK DQKGGLHSLQ EIRVCEIHED SSTRGSRHFY YDGELFLSQN
  121 LETQESTVPQ SSRAQTLAMN VTNFWKEDAM KTKTHYRAMQ ADCLQKLQRY LKSGVAIRRT
  181 VPPMVNVTCS EVSEGNITVT CRASSFYPRN ITLTWRQDGV SLSHNTQQWG DVLPDGNGTY
  241 QTWVATRIRQ GEEQRFTCYM EHSGNHGTHP VPSGKALVLQ SQRTDFPYVS AAMPCFVIII
  301 ILCVPCCKKK TSAAEGP

SEQ. ID. NO. 11    MICB
    1 PHSLRYNLMV LSQDGSVQSG FLAEGHLDGQ PFLRYDRQKR RAKPQGQWAE DVLGAETWDT
   61 ETEDLTENGQ DLRRTLTHIK DQKGGLHSLQ EIRVCEIHED SSTRGSRHFY YNGELFLSQN
  121 LETQESTVPQ SSRAQTLAMN VTNFWKEDAM KTKTHYRAMQ ADCLQKLQRY LKSGVAIRRT
  181 VPPMVNVTCS EVSEGNITVT CRASSFYPRN ITLTWRQDGV SLSHNTQQWG DVLPDGNGTY
  241 QTWVATRIRQ GEEQKFTCYM EHSGNHGTHP VPSGKALVLQ SQRTDFPYVS AAMPCFVIII
  301 ILCVPCCKKK TSAAEGP

SEQ. ID. NO. 12    MICB
    1 PHSLRYNLMV LSQDGSVQSG FLAEGHLDGQ PFLRYDRQKR RAKPQGQWAE DVLGAETWDT
   61 ETEDLTENGQ DLRRTLTHIK DQKGGLHSLQ EIRVCEIHED SSTRGSRHFY YNGELFLSQN
  121 LETQESTVPQ SSRAQTLAMN VTNFWKEDAM KTKTHYRAMQ ADCLQKLQRY LKSGVAIRRT
  181 VPPMVNVTCS EVSEGNITVT CRASSFYPRN ITLTWRQDGV SLSHNTQQWG DVLPDGNGTY
  241 QTWVATRIRQ GEEQRFTCYM EHSGNHGTHP VPSGKALVLQ SQRTDFPYVS AAMPCFVIII
  301 ILCVPCCKKK TSAAEGP

SEQ. ID. NO. 13    MICA
    EPHSLRYNLT VLSWDGSVQS GFLTEVHLDG QPFLRCDRQK CRAKPQGQWA EDVLGNKTWD
    RETRDLTGNG KDLRMTLAHI KDQKEGLHSL QEIRVCEIHE DNSTRSSQHF YYDGELFLSQ
    NLETKEWTMP QSSRAQTLAM NVRNFLKEDA MKTKTHYHAM HADCLQELRR YLKSGVVLRR
    TVPPMVNVTR SEASEGNITV TCRASGFYPW NITLSWRQDG VSLSHDTQQW GDVLPDGNGT
    YQTWVATRIC QGEEQRFTCY MEHSGNHSTH PVPSGK
```

Figure 7B

```
SEQ. ID. NO.14    DNA FOR SEQ. ID. NO. 13 MICA
     GCTAGCGCTG AGAGGGTGGC GACGTCGGGG CCATGGGGCT GGGCCCGGTC TTCCTGCTTC
     TGGCTGGCAT CTTCCCTTTT GCACCTCCGG GAGCTGCTGC TGAGCCCCAC AGTCTTCGTT
     ATAACCTCAC GGTGCTGTCC TGGGATGGAT CTGTGCAGTC AGGGTTTCTC ACTGAGGTAC
     ATCTGGATGG TCAGCCCTTC CTGCGCTGTG ACAGGCAGAA ATGCAGGGCA AAGCCCCAGG
     GACAGTGGGC AGAAGATGTC CTGGGAAATA AGACATGGGA CAGAGAGACC AGGGACTTGA
     CAGGGAACGG AAAGGACCTC AGGATGACCC TGGCTCATAT CAAGGACCAG AAAGAAGGCT
     TGCATTCCCT CCAGGAGATT AGGGTCTGTG AGATCCATGA AGACAACAGC ACCAGGAGCT
     CCCAGCATTT CTACTACGAT GGGGAGCTCT TCCTCTCCCA AACCTGGAGA CTAAGGAATG
     GACAATGCCC CAGTCCTCCA GAGCTCAGAC CTTGGCCATG AACGTCAGGA ATTTCTTGAA
     GGAAGATGCC ATGAAGACCA AGACACACTA TCACGCTATG CATGCAGACT GCCTGCAGGA
     ACTACGGCGA TATCTAAAAT CCGGCGTAGT CCTGAGGAGA ACAGTGCCCC CCATGGTGAA
     TGTCACCCGC AGCGAGGCCT CAGAGGGCAA CATTACCGTG ACATGCAGGG CTTCTGGCTT
     CTATCCCTGG AATATCACAC TGAGCTGGCG TCAGGATGGG GTATCTTTGA GCCACGACAC
     CCAGCAGTGG GGGGATGTCC TGCCTGATGG GAATGGAACC TACCAGACCT GGGTGGCCAC
     CAGGATTTGC CAAGGAGAGG AGCAGAGGTT CACCTGCTAC ATGGAACACA GCGGGAATCA
     CAGCACTCAC CCTGTGCCCT CTGGGAAATA AAAGCTT

SEQ. ID. NO. 15    AV1401 5'-
     TATGAAATACCTGCTGCCGACCGCTGCTGCTGGTCTGCTGCTCCTCGCTGCCCAGCC-3'

SEQ. ID. NO. 16    AV1402 5'-
     CATGGGCTGGGCAGCGAGGAGCAGCAGACCAGCAGCAGCGGTCGGCAGCAGGTATTTCA-3'

SEQ. ID. NO. 17    AV1445 5'-
     CATGCATCATCACCATCACCACCTCGAGGAATTCAAGCTTGGATCCGC-3'

SEQ. ID. NO. 18    AV1446 5'-
     TCAGCGGATCCAAGCTTGAATTCCTCGAGGTGGTGATGGTGATGATG-3'

SEQ. ID. NO. 19    AV1466 5'-
     TTTTTTGCTAGCGCTGAGAGGGTGGCGACGTC-3'

SEQ. ID. NO. 20    AV1448 5'-
     CTTTCCAAGCTTTTATTTCCCAGAGGGCACAGGGTG-3'

SEQ. ID. NO. 21    AV1447 5'-
     TCCCTCCTCGAGGAAAACTTGTACTTTCAAGGCGAGCCCCACAGTCTTCGTTATAACC-3'

SEQ. ID. NO. 22    AV1408 5'-
     CCCCCCGGATCCATGATTACTCATGGTTGTTATACCCG-3'

SEQ. ID. NO. 23    AV1409 5'-
     CCCCCCAAGCTTATTCTACACAAACCGCATAGAC-3'

SEQ. ID. NO. 24    AV1602 5'-
     TTTTTTCTCGAGGTGGTGATGGTGATGATGTCGGCCTTCAATACCGCCGCTGGCCTTGGTTTGATC-3'

SEQ. ID. NO. 25    AV1603 5'-
     CCCCCCCATATGATTACTCATGGTTGTTATACCCGG-3'

SEQ. ID. NO. 26    KK43 5'-
     AAAAAACTCGAGGAAAACTTGTACTTTCAAGGCACAGTGCCACCCATGGTGAATGTCACCCGCAG-3'
```

Figure 7C

SEQ. ID. NO. 27  KK44 5'-
    ATATATAAGCTTTTATTTCCCAGAGGGCAC-3'

SEQ. ID. NO. 28  KK52 5'-
    TTTTTTCGTCTCTCATGATTACTCATGGT-3'

SEQ. ID. NO. 29  KK45 5'-
    ATATACATACAGTCGACCAGGTTGGGGGCGGTATTGAAGGCCGACATC-3'

SEQ. ID. NO. 30  AV1466 5'-
    TTTTTTGCTAGCGCTGAGAGGGTGGCGACGTC-3'

SEQ. ID. NO. 31  AV1448 5'-
    CTTTCCAAGCTTTTATTTCCCAGAGGGCACAGGGTG-3'

SEQ. ID. NO. 32  AV1490 5'-
    AATCACAGCACTCACCCTGTGCCC-3'

SEQ. ID. NO. 33  AV1489 5'-
    TCCCTTCGTCTCTGGTCGGATACGCTGTCGAACTTTTCGATC-3'

SEQ. ID. NO. 34  AV1493 5'-
    P-GAATCCTGGTGGCCACCCAGGTCTGG-3'

SEQ. ID. NO. 35  AV1494 5'-
    P-GAGACGACAAACGTCTCTTGCTACATGGAACACAGCGGGAATC-3'

SEQ. ID. NO. 36  AV1826
    5'-
    GATTAGTGGTGGCAGTGGCGGCGGTAGTCATCATCACCACCATCACCACCATCACCACAGCGGCGGCAGCG
    GTGGCGGT-3'

SEQ. ID. NO. 37  AV1827 5'-
    AGCAACCGCCACCGCTGCCGCCGCTGTGGTGATGGTGGTGATGGTGGTGATGATGACTACCGCCGCCACTG
    CCACCACT-3'

SEQ. ID. NO. 38  pKK35
    SGGSGGGSHHHHHHHHHHSGGSGGG

SEQ. ID. NO:39  AV1478
    5'-P-AGTCAGGGTTTCTCACTGAGGTACATCTGG-3'

SEQ. ID. NO:40  AV1479
    5'-P-GCACAGATCCATCCCAGGACAGCACCGTGAG-3

SEQ. ID. NO:41  AV1486
    5'-P-CATCATCATGAGCCCCACAGTCTTCGTTATAACC-3'

SEQ. ID. NO:42  AV1487
    5'-P-GTGGTGGTGAGCAGCAGCTCCCGGAGGTGCAAAAGGG-3'

SEQ. ID. NO:43  pKK36
    SRGDHPRTQ

Figure 7D

SEQ. ID. NO:44    AV1830
    5'- CACCTCTCGGGGCGATCACCCTCGCACCCAG-3'

SEQ. ID. NO:45    AV1831
    5'- TCACCTGGGTGCGAGGGTGATCGCCCCGAGA-3'

SEQ. ID. NO:46    pKK37
    RTSRGDHPRTQ

SEQ. ID. NO:47    AV1832
    5'-CACCAGGACATCTCGGGGCGATCACCCTCGCACCCAG-3'

SEQ. ID. NO:48    AV1833
    5'-TCACCTGGGTGCGAGGGTGATCGCCCCGAGATGTCCT-3'

SEQ. ID. NO:49    pKK38
    RVPRGDSDLT

SEQ. ID. NO:50    AV1834
    5'-CACCAGGGTGCCTCGGGGCGATAGCGATCTGACC-3'

SEQ. ID. NO:51    AV1835
    5'- TCACGGTCAGATCGCTATCGCCCCGAGGCACCCT-3'

SEQ. ID. NO:52    pKK39
    RSARGDSDHR

SEQ. ID. NO:53    AV1836
    5'-CACCAGGAGCGCCCGGGGCGATAGCGATCACCGG-3'

SEQ. ID. NO:54    AV1837
    5'- TCACCCGGTGATCGCTATCGCCCCGGGCGCTCCT-3'

SEQ. ID. NO:55    pKK40
    VTRGDTFTQS

SEQ. ID. NO:56    AV1838
    5'- CACCGTGACACGGGGCGATACTTTCACACAGTCC-3'

SEQ. ID. NO:57    AV1839
    5'- TCACGGACTGTGTGAAAGTATCGCCCCGTGTCAC-3'

SEQ. ID. NO:58    pKK41
    RGDTFTQS

SEQ. ID. NO:59    AV1840
    5'- CACCCGGGGCGATACTTTCACACAGTCC-3'

SEQ. ID. NO:60    AV1841
    5'- TCACGGACTGTGTGAAAGTATCGCCCCG-3'

SEQ. ID. NO:61    pKK42
    HLARGDDLTY

Figure 7E

```
SEQ. ID. NO:62    AV1842
    5'- CACCCACCTGGCACGGGGCGATGACCTGACATAC-3'

SEQ. ID. NO:63    AV1843
    5'- TCACGTATGTCAGGTCATCGCCCCGTGCCAGGTG-3'

SEQ. ID. NO:64    pKK44
    SGGSGGGSTSRGDHPRTQSGGSGGG

SEQ. ID. NO:65    AV1854
    5'-CACCAGTGGTGGCAGTGGCGGCGGTAGTACATCTCGGGGCGATCACC
    CTCGCACCCAGAGCGGCGGCAGCGGTGGCGGT-3'

SEQ. ID. NO:66    AV1855
    5'TCACACCGCCACCGCTGCCGCCGCTCTGGGTGCGAGGGTGATCGCCCCGA
    GATGTACTACCGCCGCCACTGCCACCACT-3'

SEQ. ID. NO:67    pKK45
    SGGSGGGSRVPRGDSDLTSGGSGGG

SEQ. ID. NO:68    AV1856
    5'-
    CACCAGTGGTGGCAGTGGCGGCGGTAGTAGGGTGCCTCGGGGCGATAGCGATCTGACCAGCGGCGGCAGCG
    GTGGCGGT-3'

SEQ. ID. NO:69    AV1857
    5'-
    TCACACCGCCACCGCTGCCGCCGCTGGTCAGATCGCTATCGCCCCGAGGCACCCTACTACCGCCGCCACTG
    CCACCACT-3'

SEQ. ID. NO:70    pKK46
    SGGSGGGSVTRGDTFTQSSGGSGGG

SEQ. ID. NO:71    AV1858
    5'-
    CACCAGTGGTGGCAGTGGCGGCGGTAGTGTGACACGGGGCGATACTTTCACACAGTCCAGCGGCGGCAGCG
    GTGGCGGT-3'

SEQ. ID. NO:72    AV1859
    5'-
    TCACACCGCCACCGCTGCCGCCGCTGGACTGTGTGAAAGTATCGCCCCGTGTCACACTACCGCCGCCACTG
    CCACCACT-3'

SEQ. ID. NO:73    pKK47
    SGGSGGGSHLARGDDLTYSGGSGGG

SEQ. ID. NO:74   AV1860
    5'-
    CACCAGTGGTGGCAGTGGCGGCGGTAGTCACCTGGCACGGGGCGATGACCTGACATACAGCGGCGGCAGCG
    GTGGCGGT-3'

SEQ. ID. NO:75  AV1861
    5'-
    TCACACCGCCACCGCTGCCGCCGCTGTATGTCAGGTCATCGCCCCGTGCCAGGTGACTACCGCCGCCACTG
    CCACCACT-3'
```

Figure 7F

SEQ. ID. NO:76   pKK48   pKK128
SGGSGGGSTSRGDHPRTQSGGSGGG

SEQ. ID. NO:77   AV1864
5'-
GATTAGTGGTGGCAGTGGCGGCGGTAGTACATCTCGGGGCGATCACCCTCGCACCCAGAGCGGCGGCAGCG
GTGGCGGT-3'

SEQ. ID. NO:78   AV1865
5'-
AGCAACCGCCACCGCTGCCGCCGCTCTGGGTGCGAGGGTGATCGCCCCGAGATGTACTACCGCCGCCACTG
CCACCACT-3'

SEQ. ID. NO:79   pKK49
SGGSGGGSRVPRGDSDLTSGGSGGG

SEQ. ID. NO:80   AV1866
5'-
GATTAGTGGTGGCAGTGGCGGCGGTAGTAGGGTGCCTCGGGGCGATAGCGATCTGACCAGCGGCGGCAGCG
GTGGCGGT-3'

SEQ. ID. NO:81   AV1867
5'-
AGCAACCGCCACCGCTGCCGCCGCTGGTCAGATCGCTATCGCCCCGAGGCACCCTACTACCGCCGCCACTG
CCACCACT-3'

SEQ. ID. NO:82   pKK50   pKK129   pKK131
SGGSGGGSVTRGDTFTQSSGGSGGG

SEQ. ID. NO:83   AV1868
5'-
GATTAGTGGTGGCAGTGGCGGCGGTAGTGTGACACGGGGCGATACTTTCACACAGTCCAGCGGCGGCAGCG
GTGGCGGT-3'

SEQ. ID. NO:84   AV1869
5'-
AGCAACCGCCACCGCTGCCGCCGCTGGACTGTGTGAAAGTATCGCCCCGTGTCACACTACCGCCGCCACTG
CCACCACT-3'

SEQ. ID. NO:85   pKK51   pKK130
SGGSGGGSHLARGDDLTYSGGSGGG

SEQ. ID. NO:86   AV1870
5'-
GATTAGTGGTGGCAGTGGCGGCGGTAGTCACCTGGCACGGGGCGATGACCTGACATACAGCGGCGGCAGCG
GTGGCGGT-3'

SEQ. ID. NO:87   AV1871
5'-
AGCAACCGCCACCGCTGCCGCCGCTGTATGTCAGGTCATCGCCCCGTGCCAGGTGACTACCGCCGCCACTG
CCACCACT-3'

SEQ. ID. NO:88   AV1873
5'-P- TTAATTAACGTCTCATGCAGGGCTTCTGGCTTCTATCCCTG-3'

Figure 7G

SEQ. ID. NO:89    AV1872
    5'-P- ACGTCTCGATTCACCATGGGGGGCACTGTTCTCCTC-3'

SEQ. ID. NO:90    pKK52
    TSRGDHPRTQ

SEQ. ID. NO:91    AV1874
    5'- GAATACAAGCCGAGGTGACCACCCACGTACACAA-3'

SEQ. ID. NO:92    AV1875
    5'- TGCATTGTGTACGTGGGTGGTCACCTCGGCTTGT-3'

SEQ. ID. NO:93    pKK53
    GSRGDSLIMH

SEQ. ID. NO:94    AV1876
    5'- GAATGGTTCACGAGGTGACTCATTGATTATGCAC-3'

SEQ. ID. NO:95    AV1877
    5'- TGCAGTGCATAATCAATGAGTCACCTCGTGAACC-3'

SEQ. ID. NO:96    pKK54
    RVPRGDSDLT

SEQ. ID. NO:97    AV1878
    5'- GAATCGAGTACCACGAGGTGACTCAGATTTGACT-3'

SEQ. ID. NO:98    AV1879
    5'- TGCAAGTCAAATCTGAGTCACCTCGTGGTACTCG-3'

SEQ. ID. NO:99    pKK55
    VTRGDTFTQS

SEQ. ID. NO:100    AV1880
    5'- GAATGTAACACGAGGTGACACATTCACTCAGAGC-3'

SEQ. ID. NO:101    AV1881
    5'- TGCAGCTCTGAGTGAATGTGTCACCTCGTGTTAC-3'

SEQ. ID. NO:102    pKK56
    HLARGDDLTY

SEQ. ID. NO:103    AV1882
    5'- GAATCACTTGGCACGAGGTGACGATCTCACATAC-3'

SEQ. ID. NO:104    AV1883
    5'- TGCAGTATGTGAGATCGTCACCTCGTGCCAAGTG-3'

SEQ. ID. NO:105    pKK84
    YQSWRYSQ

SEQ. ID. NO:106    AV1906
    5'- GAATTACCAGTCTTGGCGTTACTCTCAG-3'

Figure 7H

SEQ. ID. NO:107    AV1907
    5'- TGCACTGAGAGTAACGCCAAGACTGGTA-3'

SEQ. ID. NO:108    AV1493
    5'-P-GAATCCTGGTGGCCACCCAGGTCTGG-3'

SEQ. ID. NO:109    AV1494
    5'-P-GAGACGACAAACGTCTCTTGCTACATGGAACACAGCGGGAATC-3'

SEQ. ID. NO: 110        AV1908
    5'-
    GATTTCCGGAGGTTCTGGAGGTGGCTCGGTAACCCGAGGAGACACCTTTACCCAAAGTTCAGGAGGTTCAG
    GAGGTGGA-3'

SEQ. ID. NO: 111   AV1909
    5'-
    AGCATCCACCTCCTGAACCTCCTGAACTTTGGGTAAAGGTGTCTCCTCGGGTTACCGAGCCACCTCCAGAA
    CCTCCGGA-3'

SEQ. ID. NO:112    AV1887
    5'-CCTCCGAATTCGGATCCTAGGCGGCTCCTTATTTGTTTGTGAATATCAAGGCC-3'

SEQ. ID. NO:113    AV1888
    5'-CCCTCCAAGCTTAAGACTCCTTATTACGCAGTATG-3'

SEQ. ID. NO:114    TEND
    GAATTCATGAAAAAATTATTATTCGCAATTCCTTTAGTGGTACCTTTCTATTCTCACTCGGACTACAAGGA
    TGACGACGATAAGCAATTGGAACCAGCGCCATCTTGCGTTACCCTGTACCAGTCTTGGCGTTACTCTCAGG
    CTGACAACGGTTGCGCAGAAACGGTTACCGTAAAAGTGGTATACGAAGACGACACCGAGGGCCTGTGCTAC
    GCAGTTGCCCCGGGTCAGATCACCACTGTTGGTGACGGCTACATCGGCTCTCACGGTCACGCTCGGTATCT
    GGCTCGTTGCCTAGG

SEQ. ID. NO:115    TEND-3A
    GAATTCATGAAAAAATTATTATTCGCAATTCCTTTAGTGGTACCTTTCTATTCTCACTCGGACTACAAGGA
    TGACGACGATAAGCAATTGGAACCAGCGCCATCTTGCGTTACCCTGACATCACGAGGCGACCACCCACGCA
    CCCAGGCTGACAACGGTTGCGCAGAAACGGTTACCGTAAAAGTGGTATACGAAGACGACACCGAGGGCCTG
    TGCTACGCAGTTGCCCCGGGTCAGATCACCACTGTTGGTGACGGCTACATCGGCTCTCACGGTCACGCTCG
    GTATCTGGCTCGTTGCCTAGG

SEQ. ID. NO:116    TEND-3B
    GAATTCATGAAAAAATTATTATTCGCAATTCCTTTAGTGGTACCTTTCTATTCTCACTCGGACTACAAGGA
    TGACGACGATAAGCAATTGGAACCAGCGCCATCTTGCGTTACCCTGGGCTCACGAGGCGACTCCCTCATCA
    TGCACGCTGACAACGGTTGCGCAGAAACGGTTACCGTAAAAGTGGTATACGAAGACGACACCGAGGGCCTG
    TGCTACGCAGTTGCCCCGGGTCAGATCACCACTGTTGGTGACGGCTACATCGGCTCTCACGGTCACGCTCG
    GTATCTGGCTCGTTGCCTAGG

SEQ. ID. NO:117    TEND-5A
    GAATTCATGAAAAAATTATTATTCGCAATTCCTTTAGTGGTACCTTTCTATTCTCACTCGGACTACAAGGA
    TGACGACGATAAGCAATTGGAACCAGCGCCATCTTGCGTTACCCTGGTAACACGAGGCGACACCTTCACGC
    AGTCCGCTGACAACGGTTGCGCAGAAACGGTTACCGTAAAAGTGGTATACGAAGACGACACCGAGGGCCTG
    TGCTACGCAGTTGCCCCGGGTCAGATCACCACTGTTGGTGACGGCTACATCGGCTCTCACGGTCACGCTCG
    GTATCTGGCTCGTTGCCTAGG

Figure 7I

SEQ. ID. NO:118   TEND-5B
   GAATTCATGAAAAAATTATTATTCGCAATTCCTTTAGTGGTACCTTTCTATTCTCACTCGGACTACAAGGA
   TGACGACGATAAGCAATTGGAACCAGCGCCATCTTGCGTTACCCTGCACCTGGCACGAGGCGACGATCTTA
   CCTACGCTGACAACGGTTGCGCAGAAACGGTTACCGTAAAAGTGGTATACGAAGACGACACCGAGGGCCTG
   TGCTACGCAGTTGCCCCGGGTCAGATCACCACTGTTGGTGACGGCTACATCGGCTCTCACGGTCACGCTCG
   GTATCTGGCTCGTTGCCTAGG

SEQ. ID. NO:119   TEND-HIS8
   GAATTCATGAAAAAATTATTATTCGCAATTCCTTTAGTGGTACCTTTCTATTCTCACTCGGACTACAAGGA
   TGACGACGATAAGCAATTGGAACCAGCGCCATCTTGCGTTACCCTGCACCACCACCATCACCATCATCATT
   CACAAGCTGACAACGGTTGCGCAGAAACGGTTACCGTAAAAGTGGTATACGAAGACGACACCGAGGGCCTG
   TGCTACGCAGTTGCCCCGGGTCAGATCACCACTGTTGGTGACGGCTACATCGGCTCTCACGGTCACGCTCG
   GTATCTGGCTCGTTGCCTAGG

SEQ. ID. NO:120   AV1897
   5'-CTTCCCGAATTCATGACAGTGCCACCCATGGTGAATGTCAC-3'

SEQ. ID. NO:121   AV1898
   5'-TTTCTTCGTCTCACTAGTTTCCCAGAGGGCACAGGGTGAGTG-3'

SEQ. ID. NO:122   KK69
   5'-CTTCCCGAATTCATGACAGTGCCCCCCATGGTGAATACAAG-3'

SEQ. ID. NO:123   KK70
   5'-CTTCCCGAATTCATGACAGTGCCCCCCATGGTGAATGGTTCA-3'

SEQ. ID. NO:124   KK71
   5'-CTTCCCGAATTCATGACAGTGCCCCCCATGGTGAATCGAGTA-3'

SEQ. ID. NO:125   KK72 =
   5'- CTTCCCGAATTCATGACAGTGCCCCCCATGGTGAATGTAACA-3'

SEQ. ID. NO:126   KK73
   5'-CTTCCCGAATTCATGACAGTGCCCCCCATGGTGAATCACTTG-3'

Figure 7J

NON-NATURAL MIC PROTEINS

RELATED APPLICATIONS

This application is a continuation-in-part application of U.S. application Ser. No. 12/982,827, filed Dec. 30, 2010, which claims priority from U.S. Provisional Application No. 61/291,749, filed Dec. 31, 2009, both of which are hereby incorporated by reference in their entireties.

STATEMENT OF GOVERNMENT SUPPORT

This invention was made, in part, with government support under National Institutes of Health (NIH) Small Business Innovation Research (SBIR) grant number 1R43088979 awarded by the National Institute of Allergy and Infectious Diseases. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 29, 2011, is named CA2173.txt and is 67,085 bytes in size.

FIELD OF THE INVENTION

The instant invention relates generally to non-natural protein molecules that can recruit and activate NK cells, and more specifically to non-natural, monomeric, soluble, mammalian MHC class I chain-related (MIC) molecules modified within the α3 domain to contain a heterologous peptide that binds a target molecule on target cell.

BACKGROUND OF THE INVENTION

Natural killer (NK) cells and certain (CD8+ αβ and γδ) T-cells of the immunity system have important roles in humans and other mammals as first-line, innate defense against neoplastic and virus-infected cells (Cerwenka, A., and L. L. Lanier. 2001. NK cells, viruses and cancer. Nat. Rev. Immunol. 1:41-49). NK cells and certain T-cells exhibit on their surfaces NKG2D, a prominent, homodimeric, surface immunoreceptor responsible for recognizing a target cell and activating the innate defense against the pathologic cell (Lanier, L L, 1998. NK cell receptors. Ann. Rev. Immunol. 16: 359-393; Houchins J P et al. 1991. DNA sequence analysis of NKG2, a family of related cDNA clones encoding type II integral membrane proteins on human NK cells. J. Exp. Med. 173: 1017-1020; Bauer, S et al., 1999. Activation of NK cells and T cells by NKG2D, a receptor for stress-inducible MICA. Science 285: 727-730). The human NKG2D molecule possesses a C-type lectin-like extracellular domain that binds to its cognate ligands, the 84% sequence identical or homologous, monomeric MICA [soluble form of MICA set forth in SEQ ID NOs: 1-6 and 13] and MICB [full protein of MICB set forth in SEQ ID NOs: 7-12], polymorphic analogs of the Major Histocompatibility Complex (MHC) Class I chain-related glycoproteins (MIC) (Weis et al. 1998. The C-type lectin superfamily of the immune system. Immunol. Rev. 163: 19-34; Bahram et al. 1994. A second lineage of mammalian MHC class I genes. PNAS 91:6259-6263; Bahram et al. 1996a. Nucleotide sequence of the human MHC class I MICA gene. Immunogenetics 44: 80-81; Bahram and Spies T A. 1996. Nucleotide sequence of human MHC class I MICB cDNA. Immunogenetics 43: 230-233). Non-pathologic expression of MICA and MICB is restricted to intestinal epithelium, keratinocytes, endothelial cells and monocytes, but aberrant surface expression of these MIC proteins occurs in response to many types of cellular stress such as proliferation, oxidation and heat shock and marks the cell as pathologic (Groh et al. 1996. Cell stress-regulated human MHC class I gene expressed in GI epithelium. PNAS 93: 12445-12450; Groh et al. 1998. Recognition of stress-induced MHC molecules by intestinal γδT cells. Science 279: 1737-1740; Zwirner et al. 1999. Differential expression of MICA by endothelial cells, fibroblasts, keratinocytes and monocytes. Human Immunol. 60: 323-330). Pathologic expression of MIC proteins also seems involved in some autoimmune diseases (Ravetch, J V and Lanier L L. 2000. Immune Inhibitory Receptors. Science 290: 84-89; Burgess, S J. 2008. Immunol. Res. 40: 18-34). The differential regulation of NKG2D ligands, the polymorphic MICA (>50 alleles, see for examples SEQ ID NOS: 1-6 and 13 of FIG. 6) and MICB (>13 alleles, see for examples SEQ ID NOS: 7-12 of FIG. 6), is important to provide the immunity system with a means to identify and respond to a broad range of emergency cues while still protecting healthy cells from unwanted attack (Stephens H A, (2001) MICA and MICB genes: can the enigma of their polymorphism be resolved? Trends Immunol. 22: 378-85; Spies, T. 2008. Regulation of NKG2D ligands: a purposeful but delicate affair. Nature Immunol. 9: 1013-1015).

Viral infection is a common inducer of MIC protein expression and identifies the viral-infected cell for NK or T-cell attack (Groh et al. 1998; Groh et al. 2001. Co-stimulation of CD8+ αβT-cells by NKG2D via engagement by MIC induced on virus-infected cells. Nat. Immunol. 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape the wrath of the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. J. Exp. Med. 197:1245-1253; Stern-Ginossar et al., (2007) Host immune system gene targeting by viral miRNA. Science 317: 376-381; Stern-Ginossar et al., (2008) Human microRNAs regulate stress-induced immune responses mediated by the receptor NKG2D. Nature Immunology 9: 1065-73; Slavuljica, I A Busche, M Babic, M Mitrovic, I Gagparovic, D Cekinovic, E Markova Car, E P Pugel, A Cikovic, V J Lisnic, W J Britt, U Koszinowski, M Messerle, A Krmpotic and S Jonjic. 2010. Recombinant mouse cytomegalovirus expressing a ligand for the NKG2D receptor is attenuated and has improved vaccine properties. J. Clin. Invest. 120: 4532-4545).

In spite of their stress, many malignant cells, such as those of lung cancer and glioblastoma brain cancer, also avoid the expression of MIC proteins and as a result may be particularly aggressive as they too escape the innate immunity system (Busche, A et al. 2006, NK cell mediated rejection of experimental human lung cancer by genetic over expression of MHC class I chain-related gene A. Human Gene Therapy 17: 135-146; Doubrovina, E S, M M Doubrovin, E Vider, R B Sisson, R J O'Reilly, B Dupont, and Y M Vyas, 2003. Evasion from NK Cell Immunity by MHC Class I Chain-Related Molecules Expressing Colon Adenocarcinoma (2003) J. Immunology 6891-99; Friese, M. et al. 2003. MICA/NKG2D-mediated immunogene therapy of experimental gliomas. Cancer Research 63: 8996-9006; Fuertes, M B, M V Girart, L L Molinero, C I Domaica, L E Rossi, M M Barrio, J Mordoh, G A Rabinovich and N W Zwirner. (2008) Intracellular Retention of the NKG2D Ligand MHC Class I Chain-Related Gene A in Human Melanomas Confers Immune Privilege and Prevents NK Cell-Mediated Cytotoxicity. J. Immunology, 180: 4606-4614).

SUMMARY OF THE INVENTION

This invention describes soluble, monomeric, non-natural protein molecules that can recruit and activate NK cells and certain T-cells to attack specific cellular target cells by, after administration to a mammal, attaching the NKG2D-binding portions of MICA or MICB protein, i.e., their α1-α2 platform domain, specifically to the intended target molecule or molecules on the cellular target via a molecular targeting motif of the non-natural protein molecules of the invention.

Accordingly, in one aspect of the invention there are provided non-natural, monomeric, soluble, mammalian MHC class I chain-related (MIC) molecules containing an α1-α2 platform domain attached to a targeting motif, wherein the targeting motif contains a MIC α3 domain and one or more heterologous peptides, wherein the heterologous peptide(s) is/are inserted into one or more loops of the MIC α3 domain at a non-carboxy-terminal site, and wherein the heterologous peptides direct the binding of the targeting motif to a target molecule on a target cell, thereby delivering the attached α1-α2 platform domain to the target cell. In preferred embodiments, the heterologous peptide or peptides are inserted into the MIC α3 domain within one or more sites selected from loop 1, loop 2, and loop 3. In particular embodiments, loop 1 corresponds to amino acids numbers 190-199, loop 2 corresponds to amino acid residues 221-228, and loop 3 corresponds to amino acid residues 250-258 of the α3 domain of a MIC protein selected from the group consisting of SEQ ID NOs:1-13. In certain embodiments, the MIC molecule is glycosylated.

In some embodiments of the invention non-natural MIC proteins, the α1-α2 platform domain and the α3 domain are from a human MIC protein. In particular embodiments, the α1-α2 platform domain and the α3 domain are from a human MICA protein selected from the group consisting of SEQ ID NOs:1-6, and 13. In other embodiments, the α1-α2 platform domain and the α3 domain are from a human MICB protein selected from the group consisting of SEQ ID NOs:7-12. In preferred embodiments, the MICA or MICB protein is lacking its transmembrane domain.

In certain embodiments, the α3 domain of the non-natural MIC molecule is a complete native α3 domain without a deletion. In other embodiments, the α3 domain is a native α3 domain, wherein a portion of the domain has been deleted. In some embodiments, the portion deleted from the α3 domain is adjacent to the insertion site of the heterologous peptide. In particular embodiments, the portion deleted is within 10 amino acid residues of the insertion site. In other embodiments, the portion deleted is within 9, 8, 7, 6, 5, 4, 3, 2, or 1 amino acid residue of the insertion site. In other embodiments, the α3 domain comprises a deletion, insertion, amino acid substitution, mutation, or combination thereof at site different from the insertion site.

In particular embodiments of the non-natural MIC molecules, the insertion of the heterologous peptides are within one or more solvent-exposed loops of the α3 domain. In certain embodiments, a solvent-exposed loop corresponds to amino acids numbers 190-199, 208-211, 221-228, 231-240, 250-258, or 264-266 of the α3 domain within a MIC protein selected from the group consisting of SEQ ID NOs:1-13. In preferred embodiments, the insertion is in a solvent-exposed loop corresponding to amino acids numbers 190-199, 221-228, or 250-258 of the α3 domain within a MIC protein selected from the group consisting of SEQ ID NOs:1-13. In particular embodiments, all or a portion of one or more of loop 1, loop 2, or loop 3 is deleted and replaced with the heterologous peptide. In preferred embodiments, all of one or more of loop 1, loop 2, or loop 3 is deleted, and wherein further one, two, three, four, or five additional amino acids of the α3 domain adjacent to one or both sides of the deleted loop are deleted. In more preferred embodiments, all of one or more of loop 1, loop 2, or loop 3 is deleted, and wherein further one, two, or three additional amino acids of the α3 domain adjacent to one or both sides of the deleted loop are deleted. In some embodiments, a loop and two additional amino acids from both sides of the deleted loop are deleted, resulting in a deletion corresponding to amino acids residues 188-201, 219-230, or 248-260 of an α3 domain of a MIC protein selected from the group consisting of SEQ ID NOs:1-13. In a particular aspect, loop 1 is deleted and two additional amino acids from both sides of the deleted loop are deleted, corresponding to amino acids numbers 188-201 of an α3 domain of a MIC protein selected from the group consisting of SEQ ID NOs:1-13.

In some embodiments, more than one of loop 1, loop 2, or loop 3 of a MIC molecule contains a heterologous peptide. In some embodiments, the heterologous peptides bind to the same target molecule. In one aspect, the heterologous peptides contain the same amino acid sequence. In other embodiments, the heterologous peptides bind different target molecules.

In some embodiments of the invention, the target molecule is a cell-surface molecule. In particular embodiments, the cell-surface molecule is on the surface of a malignant cell or a virus infected cell. In particular embodiments in which the target cell is malignant, the target molecule is a human epidermal growth factor receptor 2 (HER2), NK-1R, epidermal growth factor receptor (EGFR), Erb2 or melanoma antigen; antigens of LNcaP and PC-3 cancer cells; a growth factor receptor, an angiogenic factor receptor, an integrin, CD3, CD19, CD20, CD113, CD271, or an oncogene-encoded protein product, or a fragment thereof. In preferred embodiments, the target molecule is selected from the group consisting of an integrin, ErbB2, FGF1 Receptor, FGF2 Receptor, FGF3 Receptor, IGF1 Receptor, IGF2 Receptor, VEGF1 Receptor, VEGF2 Receptor, CD19, CD20, CD113, CD271, or an oncogene-encoded protein product, or a fragment thereof. In some embodiments, the target molecule is an integrin. There are 18 known α-chains and 8 known β-chains forming at least 24 distinct integrin heterodimers, many of which are involved in pathogenic cells such as cancer cells (Koistinen and Heino, 2011. Integrins in Cancer Cell Invasion. Landes Bioscience NCBI Bookshelf ID NBK6070). Such integrins include α1β1, α2β1, α3β1, α4β1, α4β7, α5β1, α6β1, α6β4, α7β1, α8β1, α9β1, α10β1, αIIbβ1, αIIbβ3, αVβ1, αVβ3, αVβ5, αVβ6, and αVβ8. In preferred embodiments, the integrin is selected from the group consisting of αVβ3, αVβ5 and α5β1. In other embodiments, the target molecule is a growth factor receptor or a cell determinant (CD) protein. In preferred embodiments the growth factor receptor or CD protein is selected from the group consisting of ErbB2, FGF1-3 Receptors, IGF1 Receptor, IGF2 Receptor, VEGF1 Receptor, VEGF2 Receptor, CD19, CD20, CD113, and CD271.

In embodiments in which the target cell is infected by a virus, the target molecule on the target cell is a phosphotidylserine, or a phosphotidylserine with an accessory protein; or a surface glycoprotein encoded by a virus, an adenovirus, a human immunodeficiency virus, a herpetic virus, a pox virus, a flavivirus, a filovirus, a hepatitis virus, a papilloma virus, cytomegalovirus, vaccinia, rotavirus, influenza, a parvo virus, West Nile virus, rabies, polyoma, rubella, distemper virus, or Japanese encephalitis virus.

In another aspect of the invention, there are provided compositions containing the non-natural MIC molecules of the invention and a carrier or excipient.

In a further aspect of the invention, there are provided nucleic acid molecules encoding the non-natural, soluble, monomeric MIC molecules of the invention. In particular embodiments, there are provided nucleic acid molecules encoding non-natural, monomeric, soluble, mammalian MHC class I chain-related (MIC) molecules containing an α1-α2 platform domain attached to a targeting motif, wherein the targeting motif contains a MIC α3 domain and one or more heterologous peptides, wherein the heterologous peptide(s) is/are inserted into one or more loops of the MIC α3 domain at a non-carboxy-terminal site, and wherein the heterologous peptides direct the binding of the targeting motif to a target molecule on a target cell, thereby delivering the attached α1-α2 platform domain to the target cell. In particular embodiments of the nucleic acid molecules encoding non-natural MIC molecules, a polynucleotide encoding heterologous peptides are inserted within the nucleic acid sequence encoding a solvent-exposed loop of the α3 domain corresponding to amino acids numbers 190-199, 208-211, 221-228, 231-240, 250-258, or 264-266 of the α3 domain within a MIC protein selected from the group consisting of SEQ ID NOs:1-13. In preferred embodiments of the nucleic acid molecules encoding non-natural MIC molecules, the heterologous peptide or peptides are inserted into the MIC α3 domain within one or more sites selected from loop 1, loop 2, and loop 3. In particular embodiments, loop 1 corresponds to amino acids numbers 190-199, loop 2 corresponds to amino acid residues 221-228, and loop 3 corresponds to amino acid residues 250-258 of the α3 domain of a MIC protein selected from the group consisting of SEQ ID NOs:1-13.

In another aspect of the invention, there are provided libraries containing non-natural MIC molecules of the invention, in which the members of a library have diverse individual target binding properties.

In still another aspect of the invention, there are provided libraries containing genes encoding the non-natural MIC molecules of the invention, in which the members of a library have diverse individual target binding properties.

In still another aspect of the invention, there are provided methods of treating a mammal suspected of having a malignancy or viral infection by administering an effective amount of the a non-natural MIC molecule of the invention to the mammal, wherein the heterologous peptides direct binding of the targeting motif to the target molecule on a malignant cell or a virus-infected cell. In certain embodiments, the non-natural MIC molecule binds a NKG2D-bearing cell and a malignant cell or a NKG2D-bearing cell and a virus-infected cell, resulting in the adhesion of the NKG2D-bearing cell to the malignant cell or the virus-infected cell. In particular embodiments, the adhering NKG2D-bearing cell destroys the viability of the malignant cell or the virus-infected cell.

BRIEF DESCRIPTION OF THE DRAWINGS

FIG. 1. shows the structure of the soluble form of human MICA. The human MICA structure represented as ribbons as solved by Pingwei Li, et al. (Nature Immunology 2, 443-451, 2001). The α1 and α2 domains provide the binding sites for the NKG2D homodimer. The α3 domain is a member of the Ig super-family and in this soluble form expressed in *E. coli* contains the C-terminus.

FIG. 2. shows a photograph of the SDS-PAGE analysis of the cytosolic ("cytosol"), cytoplasmic membrane ("Cytopl memb"), and outer membrane ("Outer memb") proteins from induced (lanes labeled "B") or un-induced (lanes labeled "A") cultures of *E. coli* harboring pKK29 detected by Coomassie blue staining or Western blotting with an antibody against human MICA. The molecular weights are indicated. The fusion of MICA α3 domain to intimin (EaeA) is expressed on the outer membrane of the *E. coli* cells induced with arabinose.

FIG. 3. A cartoon of the configuration of DNA encoding soluble MICA amino acids 1-276 in the mammalian expression vector, pc5DNA/FRT. The positions of CMV promoter, secretion signal, His-hexamer tag ("His6"; SEQ ID NO:127), "tight" loop 1 (amino acids 188-201) and loop 3 (amino acids 250-258) of α3, and the polyA tail of bgh are shown.

FIG. 4. The configuration of MICA α3-encoding DNA fused to DNA encoding a portion of M13 phage pIII. The positions of the lac promoter, $P_{lac}$, pIII secretion signal, a FLAG tag and "tight" loop 1 (amino acids 188-201) and loop 3 (amino acids 250-258) of α3 are shown.

FIG. 5. shows a schematic of a DGR-based approach for diversifying the α3 domain of human MICA.

FIG. 6. shows a schematic of the structures of EaeA and the EaeA-α3 fusion proteins displayed on the surface of *E. coli*. OM is outer membrane; D1-D3 are Ig superfamily motifs, Xa is a factor X cleavage site, and H6 is a hexa-histadine.

FIGS. 7A through 7J. provide the amino acid or nucleic acid sequences for SEQ ID NOs: 1-126.

DETAILED DESCRIPTION OF THE INVENTION

This invention describes soluble, monomeric, non-natural MIC protein molecules that can recruit and activate NK cells and certain T-cells to attack specific cellular target cells by, after administration to a mammal, binding of the NKG2D-binding portions of MICA or MICB protein, i.e. their α1-α2 platform domain (amino acids 1-85 and 86-178, for the α1 domain and the α2 domain, respectively), to the intended target molecule or molecules specifically via a targeting motif attached to α1-α2 platform domain. The targeting motif includes an α3 domain of a MICA or MICB protein and inserted heterologous peptide or peptides that bind a target molecule.

A "heterologous peptide" is a peptide that is not naturally or normally within the α3 domain. In some embodiments, the heterologous peptide is integral to one of the solvent-exposed loops of the soluble MICA or MICB α3 domain. An integral heterologous peptide can be a non-terminal component of the MIC α3 domain and direct the binding of the MICα3 domain to a target molecule. A heterologous peptide may be inserted into a α3 domain loop between two adjacent residues of the loop without deleting any of the existing loop. Alternatively, all or a portion of the loop may be deleted and replaced with the heterologous peptide. In preferred embodiments, all of the loop is deleted and replaced with the insert. In additional embodiments, all of the loop is deleted and one, two, three, four, or five additional amino acids of the α3 domain adjacent to one or both sides of the deletion site are also deleted. In preferred embodiments one, two or three residues from one or both sides of the deletion site are deleted. In certain aspects, residues corresponding to 188-201 and/or residues 250-258 of SEQ ID NOs:1-13 are deleted. In some embodiments, a portion of the loop containing one or more residues is deleted and replaced with the heterologous peptide. In certain embodiments, the portion deleted is one to three residues of the loop, or one to five amino acid residues of the loop, or even one to seven residues of the loop. In particular embodiments, the portion deleted is within 10 amino acid residues of the insertion site. In other embodiments, the portion deleted is within 9, 8, 7, 6, 5, 4, 3, 2, or 1 amino acid residue of the insertion site.

In some embodiments, the heterologous peptide may include a spacer and a binding motif. Such spacers can be a short, flexible linker peptide used to position the binding motif of the heterologous peptide so that it may bind or improve its ability to bind its target molecule.

In particular embodiments, the heterologous peptide can include a portion of a complement-determining region of a natural or recombinant antibody, another protein or peptide molecule or binding motif. In certain embodiments, the heterologous peptide is a complement-determining region of an antibody. In other embodiments, the heterologous peptide further contains an attached polysaccharide or other carbohydrate, a nucleic acid molecule such as an aptamer or synthetic analog of a nucleic acid molecule. The incorporation of a heterologous peptide or peptides results in an unnatural (or non-natural), modified or converted α3 domain of a MICA or MICB protein, which acquires the useful function of directing the targeting the α1-α2 platform based on the binding properties (e.g., cognate binding partner) of the heterologous peptide or peptides. The non-natural, monovalent molecules of the invention have the distinct advantage of not being linked or restricted to a common presenting surface and thereby can be modified, formulated and administered to a mammal as traditional biopharmaceuticals.

In preferred embodiments, more than one of loop 1, loop 2, or loop 3 of the non-natural, soluble, monomeric MIC proteins of the invention contain a heterologous peptide. In some embodiments, the heterologous peptides bind to the same target molecule. In one aspect, the heterologous peptides contain the same amino acid sequence within the binding motif. In some aspects, the target molecules may be on the same cell or the same cell type. In other aspects, the target molecules may be on different cells or cell types. In other embodiments, the heterologous peptides bind different target molecules. In some aspects, the target molecules may be on the same cell or the same cell type. In other aspects, the target molecules may be on different cells or cell types.

The modifications to the α3 domain desired include those that add or increase the specificity or sensitivity of the binding of the α3 domain to a target molecule, such as a molecule on the surface of a target cell, for example, a malignant cell or virus-infected cell. The α1-α2 platform domain is tethered to the modified targeting α3 domain and is diffusible in the intercellular or intravascular space of the mammal. Preferably the α1-α2 platform domains of the non-natural MIC proteins of the invention are at least 80% identical or homologous to a native or natural α1-α2 domain of a human MICA or MICB protein and bind an NKG2D receptor. In some embodiments, the α1-α2 platform domain is 85% identical to a native or natural α1-α2 platform domain of a human MICA or MICB protein and binds an NKG2D receptor. In other embodiments, the α1-α2 platform domain is 90%, 95%, 96%, 97%, 98%, or 99% identical to a native or natural α1-α2 platform domain of a human MICA or MICB protein and binds an NKG2D receptor. In some embodiments, the α3 domain is 85% identical (not including any modified loops) to a native or natural α3 domain of a human MICA or MICB protein. In other embodiments, the α3 domain is 90%, 95%, 96%, 97%, 98%, or 99% identical (not including any modified loops) to a native or natural α3 domain of a human MICA or MICB protein. Exemplary human MICA proteins (soluble form) include SEQ ID NOs: 1-6 and 13. Exemplary human MICB proteins (full protein) include SEQ ID NOs: 7-12.

In other embodiments, a heterologous peptide tag may be fused to the N-terminus or C-terminus of the soluble MIC protein to aid in the purification of the soluble MIC protein. Tag sequences include peptides such as a poly-histidine, myc-peptide or a FLAG tag. Such tags may be removed after isolation of the MIC molecule by methods known to one skilled in the art.

As used herein, a "soluble MIC protein", "soluble MICA" and "soluble MICB" refer to a MIC protein containing the α1, α2, and α3 domains of the MIC protein but without the transmembrane or intracellular domains. Exemplary soluble MIC proteins include amino acid residues 1-274 or 1-276 of SEQ ID NOs:1-13.

As used herein, the "full MIC protein" refers to a MIC protein containing the α1, α2, and α3 domains, the transmembrane domain, and the intracellular domain. Exemplary full MIC proteins are set forth in SEQ ID NOs:7-12.

The invention further provides a library of MIC genes or resulting soluble MIC proteins, wherein each member of the library has or exhibits a different property, such as its binding property for the target cell, resulting in a library of diverse molecules. For example, the library can contain diverse individual target binding properties representing 10 or more different binding specificities. As used herein, "diverse individual target binding properties" refers to a library of MIC proteins, in which the individual members of the library bind to a different target molecule or have different affinities or avidities for the same target molecule. In some libraries of MIC proteins, two or more members may bind the same target but may have different binding affinities or avidities.

In a further embodiment of the invention, a mammal having a malignancy or a viral infection can be treated by administering an effective amount of the soluble MIC protein to affect the malignant or viral condition. The administration of the molecule to the mammal may result in the adhesion of NKG2D-bearing NK cells or T-cells to the target malignant or virus-infected cell, wherein the NK cell or T-cell destructively attacks or destroys the target malignant or virus-infected cell. The term "destroys" as used herein in the context of the invention methods means to destroy the viability of the target cell.

As used herein, "malignancy" or "malignant conditions" refer to cancer, a class of diseases in which a group of cells display uncontrolled growth, invasion that intrudes upon and destroys adjacent tissues, and sometimes metastasis (i.e., spreading to other locations in the body via lymph or blood). In some embodiments, the malignancy is a leukemia, a lymphoma, or a myeloma. In particular embodiments, the leukemia is acute lymphoblastic (ALL) leukemia, acute myelogenous leukemia (AML), chronic lymphocytic leukemia (CLL), chronic myelogenous leukemia (CML), hairy cell leukemia, or acute monocytic leukemia (AMOL); the lymphoma is Hodgkin's lymphoma or non-Hodgkin's lymphoma; and the myeloma is multiple myeloma. In other embodiments, the malignancy is a malignant solid tumor, including breast cancer, ovarian cancer, lung cancer, prostate cancer, pancreatic cancer, brain cancer, glioblastoma, head and neck cancer, colon cancer, esophageal cancer, liver cancer, stomach cancer, uterine cancer, endocrine cancer, renal cancer, bladder cancer, or cervical cancer. In preferred embodiments, the malignancy is breast cancer, ovarian cancer, lung cancer, prostate cancer, pancreatic cancer, brain cancer, glioblastoma, head and neck cancer, or colon cancer. In more preferred embodiments, the malignancy is breast cancer.

The invention also includes the means of converting the α3 domain (for example amino acids 182-274, in SEQ ID NOs: 1-13) of a MIC protein into a specific targeting domain that can directly deliver from the intercellular space its tethered α1-α2 domain to the target cell surface in order to attract, recruit or bind the NKG2D-bearing NK cell or T-cell.

Applications of these "passive vaccines" are to destroy pathologic cells that, in spite of being pathologic, do not express the appropriate level of ligands, such as MICA or MICB, that are necessary to attract NK cells or certain T-cells. For example, only 30% of human lung cancers express MICA (Busche, A et al. 2006). Glioblastoma cells over express an NK cell inhibitory signal that prevents innate immunity attack; however, over expressing the natural MICA gene product in lung cancer or glioblastoma cells in experimental animals, restores effective NK cell attack on the cancer (Friese, M. et al. 2003).

The high resolution structure of human MICA bound to the NKG2D receptor has been solved and demonstrates that the α3 domain of MICA has no direct interaction with the NKG2D receptor (Li et al. 2001. Complex structure of the activating immunoreceptor NKG2D and its MHC class I-like ligand MICA. Nature Immunol. 2: 443-451; Protein Data Bank accession code 1HYR). The α3 domain of MICA, like that of MICB, is connected to the α1-α2 platform domain by a short, flexible linker peptide, amino acids 175-182 [of SEQ ID 1-13], and itself is positioned naturally as "spacer" between the platform and the surface of the MIC expressing cell. The 3-dimensional structures of the human MICA and MICB α3 domains are nearly identical (root-mean square distance <1 Å on 94 C-αα's) and functionally interchangeable (Holmes et al. 2001. Structural Studies of Allelic Diversity of the MHC Class I Homolog MICB, a Stress-Inducible Ligand for the Activating Immunoreceptor NKG2D. J Immunol. 169: 1395-1400).

Furthermore, the 3-dimensional structures of the MIC proteins' Ig-like α3 domains resemble that of Tendamistat, and in a sequence inverted form, that of the human tenth fibronectin domain III; both structures have served as scaffolds for engineering protein binding motifs (Pflugrath, J W, G Wiegand, R Huber, L Vértesy (1986) Crystal structure determination, refinement and the molecular model of the α-amylase inhibitor Hoe-467A. J. Molec. Biol. 189: 383-386; Koide A, Bailey C W, Huang X, Koide S. 1998. The fibronectin type III domain as a scaffold for novel binding proteins. J. Mol. Biol. 284: 1141-1151; Li, R, R H Hoess, J S Bennett and W F DeGrado (2003) Use of phage display to probe the evolution of binding specificity and affinity in integrins. Protein Engineering 16: 65-72; Lipovsek, D. et al. (2007) Evolution of an inter-loop disulfide bond in high-affinity antibody mimics based on fibronectin type III domain and selected by yeast surface display: molecular convergence with single-domain camelid and shark antibodies. J. Mol Biol 368: 1024-1041; U.S. Pat. No. 7,153,661; Protein Data Bank accession code 1TTG).

One aspect of the invention contemplates engineering specific binding properties into 1 or more of the 6 solvent-exposed loops of the α3 domain of MICA or MICB, a soluble, non-natural MIC molecule is created that after administration to a mammal can diffuse in the intravascular or intercellular space and subsequently attach with high sensitivity and specificity to a target molecule on an intended target cell and, thereby promote binding and subsequent destructive attack of the particular target cell by NKG2D-bearing NK and/or T-cells. Examples of surface accessible molecules on target malignant cells include integrins, oncogene products or fragments thereof, such as NK-1R, human epidermal growth factor 2 (Her2 or ErbB2), growth factor receptors such as Epidermal Growth Factor Receptor (EGFR), FGF Receptor3, CD30, CD19, CD20, angiogenic factor receptors such as those for vascular endothelial growth factor (VEGF) receptor and VEGF-related molecules, melanoma antigens, and antigens of LNcaP and PC-3 prostate cancer cells. The surface accessible molecules on target virus-infected cells include "inside-out" phosphotidylserine with or without accessory proteins such as apolipoprotein H, Gas6, MFG-E8; virus-encoded antigens, virus-encoded antigens of hepatitis viruses; adenoviruses; cytomegalovirus; other herpetic viruses; HIV especially p17; vaccinia; pox viruses; rotavirus; influenza; parvo viruses; West Nile virus; rabies; polyoma; papilloma viruses; rubella; distemper virus; and Japanese encephalitis virus (Balasubramanian, K and Schroit, A J. 2003. Ann. Rev. Physiol. 65: 701-734; Soares, M M, S W King & P E Thorpe. (2008) Targeting inside-out phosphatidylserine as a therapeutic strategy for viral diseases. Nature Medicine 14: 1358-62; Slavuljica et al., 2010). The present compositions can be produced by introducing specific binding motifs into the α3 domain of MICA or MICB deploying synthetic DNA, bacteriophage display or yeast or bacterial surface display technology, several of which have been deployed to create specific binding properties in Tendamistat and the human tenth fibronectin domain III (McConnell, S J and R H Hoess, (1995) Tendamistat as a Scaffold for Conformationally Constrained Phage Peptide Libraries. J. Molec. Biol 250: 460-470; Li et al. (2003); Sidhu, S. S. & S. Koide (2007) Phage display for engineering and analyzing protein interaction interfaces. Current Opinion in Struct. Biol. 17: 481-487; Lipovsek, D. et al. 2007). These methods involve making a library of α3 domain structures that are highly diversified within their solvent-exposed loops and from which to isolate the genotypes encoding those α3 domains that exhibit the desired phenotypic binding properties by selection, screening or panning, all well known to those ordinarily skilled in the art.

The diversity generating retroelements (DGR) of Miller et al. is an example of a method of generating diversity at desired amino acid positions within the loops (Medhekar, B. & J. F. Miller. 2007. Diversity-Generating Retroelements. Current Opinion in Microbiol. 10: 388-395 and U.S. Pat. No. 7,585, 957). Because the α3 domains of human MICA and MICB are comprised of about 95 amino acids (182-276) of the 276 amino acid water-soluble form, all solvent-exposed loops, for example amino acids 190-199, 208-211, 221-228, 231-240, 250-258, or 264-266 of SEQ ID NOs: 1-13, can be diversified and even expanded with inserted amino acids by homing mutagenesis deploying a synthetic Template Repeat (TR) of a length not exceeding 200 nucleotides, a length known to be operable (Guo, H et al. 2008. Diversity-Generating Retroelement Homing Regenerates Target Sequences for Repeated Rounds of Codon Rewriting and Protein Diversification. Molecular Cell 31, 813-823).

Several factors guide the creation of the DGR-based library of diversified, solvent-exposed loops of the α3 domain. First, DGRs generate diversity in defined segments of protein-encoding DNA sequences, designated as variable repeats (VRs). For some heterologous sequences to function as VRs, they are flanked at their ends by initiation of mutagenic homing (IMH) sequences. The IMH sequences serve as cis-acting sites that direct mutagenic homing and determine the 3' boundary of sequence diversification. Second, the 5' boundary of VR diversification may be determined by the extent of homology between VR and its cognate TR. Only partial homology is required and mismatches are tolerated. Third, specific sites in VR which are subject to diversification may be determined by the location of adenine residues in TR. By inserting adenine residues at appropriate locations within "synthetic" TRs, specific VR-encoded amino acid residues can be diversified. Fourth, the atd protein, the TR-encoded RNA intermediate, and the RT reverse transcriptase efficiently function in trans when expressed on a plasmid vector, pDGR, under the control of a heterologous promoter, for example, $P_{tetA}$ or $P_{bad}$. This provides a convenient means for turning on and off diversification within a bacterial cell and convenient access to the synthetic TR sequences to program the precise sites to be diversified. Furthermore, high level expression of trans-acting components results in highly efficient diversification.

Figure 5:
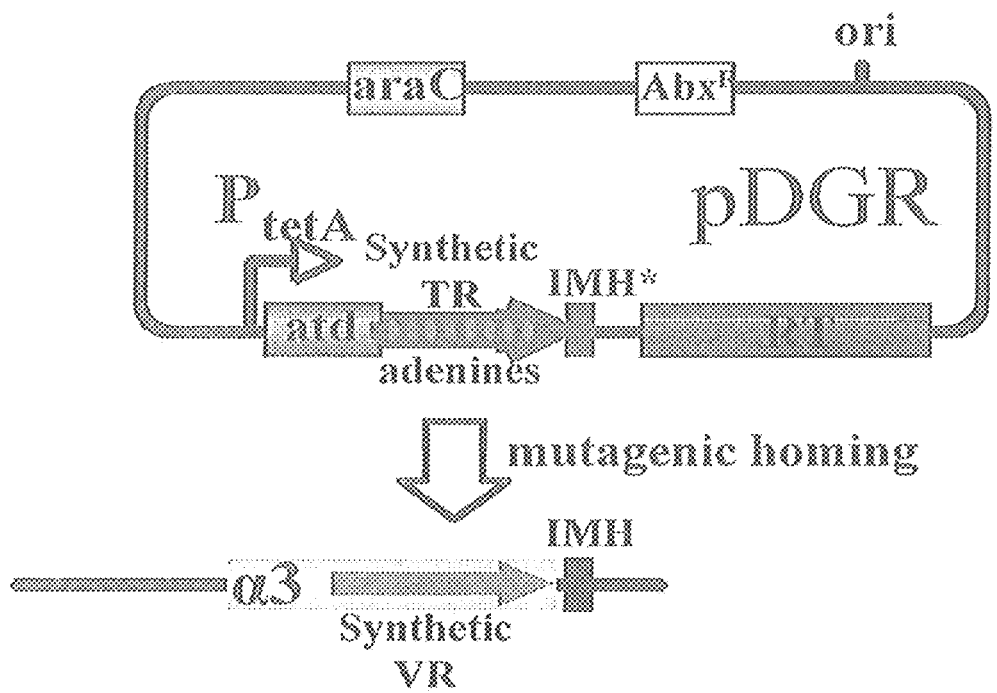

A general outline of the DGR-based approach for diversifying the α3 domain is shown in FIG. 5. The sequences to be diversified correspond to the loops of α3 domain. An IMH sequence is positioned immediately downstream from the stop codon (about AV277) of the gene encoding α3 domain, creating a "synthetic VR" which will be subject to diversification.

The synthetic VR encoding the α3 domain will be diversified by the synthetic TR on plasmid pDGR (FIG. 5). This TR element includes an IMH* and upstream sequences that are homologous to VR. The specific VR residues that will be subject to mutagenesis are precisely programmed by the placement of adenines in TR, and high densities of adenine residues can be tolerated by the system. The pDGR also includes loci which encode Atd and the RT reverse transcriptase. Atd, TR and rt are expressed from the tightly regulated tetA promoter/operator ($P_{tetA}$), which allows precise control over the diversification process by the addition or removal of anhydotetracycline.

It is instructive to consider diversifying the α3 domain via the DGR mechanism in a standard phage display format. In this case, the α3 domain is fused to a filamentous phage coat protein encoded on a phagemid vector in E. coli. VR would include solvent-exposed loops of the α3 domain, and pDGR would be designed to efficiently diversify VR at specified locations within those loops (Guo et al. 2008). Activating atd, TR, and rt expression would mutagenize VR sequences present on phagemid genomes. This would result in the creation of a library of phage, each of which presents a diversified binding protein on its surface and packages the encoding DNA. Desired specificities would be selected by binding phage to the immobilized target molecule, for example the surface exposed protein product of oncogene Her2, washing to remove nonbinding phage, and reamplification and enrichment. Further rounds of optimization of the selected phenotype could be efficiently accomplished by simply infecting E. coli containing pDGR with the selected or panned phage and repeating the steps described above. This system is capable of generating library sizes that are several orders of magnitude greater than those achieved by conventional approaches. Of equal advantage is the extraordinary ease with which successive rounds of optimization may be achieved with cumulative improvements, but without compromise of the integrity of the α3 domain scaffold.

Figure 6:
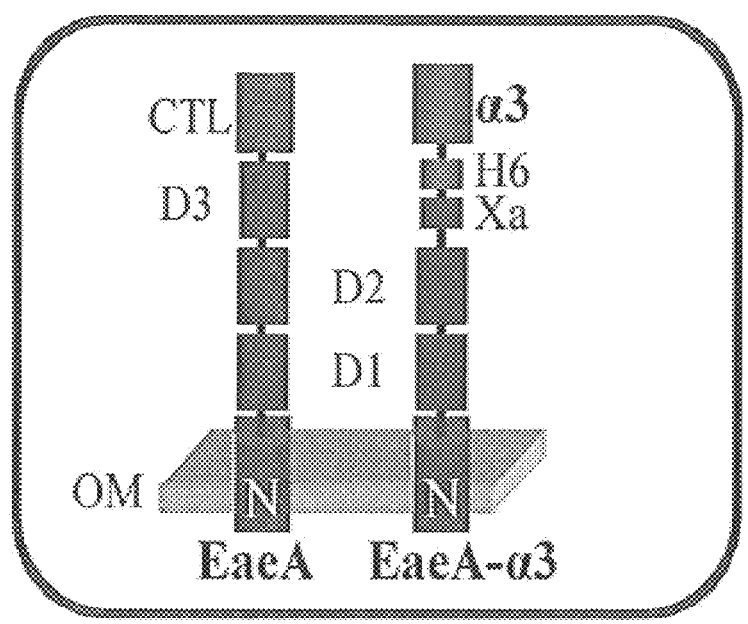

Displaying diversified proteins on the surface of bacteria, such as Escherichia coli, is an alternative approach that offers potential advantages over phage display. For example, successive rounds of optimization can be achieved without the need to make any phage or to cycle selected phage through multiple rounds of infection. And the α3 domain can be designed to be cleaved from the bacterial surface for direct biochemical or physical analyses. Although DGRs are found naturally in the genomes of over 40 bacterial species, none has been identified in E. coli. However, recently the cis and trans-acting components of a DGR from Legionella pneumophila have been shown by Miller et al to efficiently function in E. coli. Diversified α3 domains of MICA or MICB will be expressed on the surface of E. coli as fusion proteins consisting of, as a non-limiting example, the outer membrane localization and anchor domains of the EaeA intimin protein encoded by enteropathogenic E. coli (Luo Y, Frey E A, Pfuetzner R A, Creagh A L, Knoechel D G, Haynes C A, Finlay B B, Strynadka N C. (2000) Crystal structure of enteropathogenic Escherichia coli intimin-receptor complex. Nature. 405:1073-7). EaeA consists of an N-terminal segment of approximately 500 amino acids that anchors the protein to the outer membrane and is believed to form an anti-parallel β-barrel with a porin-like structure that facilitates translocation (Touze T, Hayward R D, Eswaran J, Leong J M, Koronakis V. (2004) Self-association of EPEC intimin mediated by the beta-barrel-containing anchor domain: a role in clustering of the Tir receptor. Mol Microbiol. 51:73-87). This translocation domain is followed by a series of Ig-like motifs and a C-terminal C-type lectin domain responsible for binding to the intestinal epithelial surface (FIG. 6). The elongated structure of intimin and its ability to export and anchor a heterologous protein domain to the external face of the E. coli outer membrane suggest that it is an ideal and versatile fusion partner for surface display of diversified α3 proteins (Wentzel A, Christmann A, Adams T, Kolmar H. (2001). Display of passenger proteins on the surface of Escherichia coli K-12 by the enterohemorrhagic E. coli intimin EaeA. J Bacteriol. 183: 7273-84; Adams, T M, A Wentzel, and H Kolmar (2005) Intimin-Mediated Export of Passenger Proteins Requires Maintenance of a Translocation-Competent Conformation. J. of Bacteriology, 187: 522-533).

The natural orientation of MICA and MICB is such that the C-terminus is anchored to the cell membrane (type I membrane protein). The α3 domain resides between the N-terminal α1-α2 platform and the cell membrane. However, to diversify those α3 domain loops that project away from the α1-α2 platform, the opposite orientation (e.g. type II membrane protein) is desired, that is, to attach the N-terminus the linker portion of the α3 domain in FIG. 1 to EaeA so that those loops such as those located at amino acid positions 190-199, 221-228, 250-258 of SEQ ID NOs: 1-13 are readily available for binding target molecules. Such a type II membrane protein orientation is precisely that of EaeA, FIG. 6. Furthermore, the α3 domain, like EaeA, has an Ig-like motif, so that EaeA will translocate α3 domains to the E. coli surface (Li et al. 1999. Crystal structure of the MHC class I homolog MICA, a γδT cell ligand. Immunity 10: 577-584). Indeed, the ability of EaeA to translocate heterologous passenger polypeptides has been documented in the literature (Wentzel et al. 2001; Adams et al., 2005).

Figure 2:
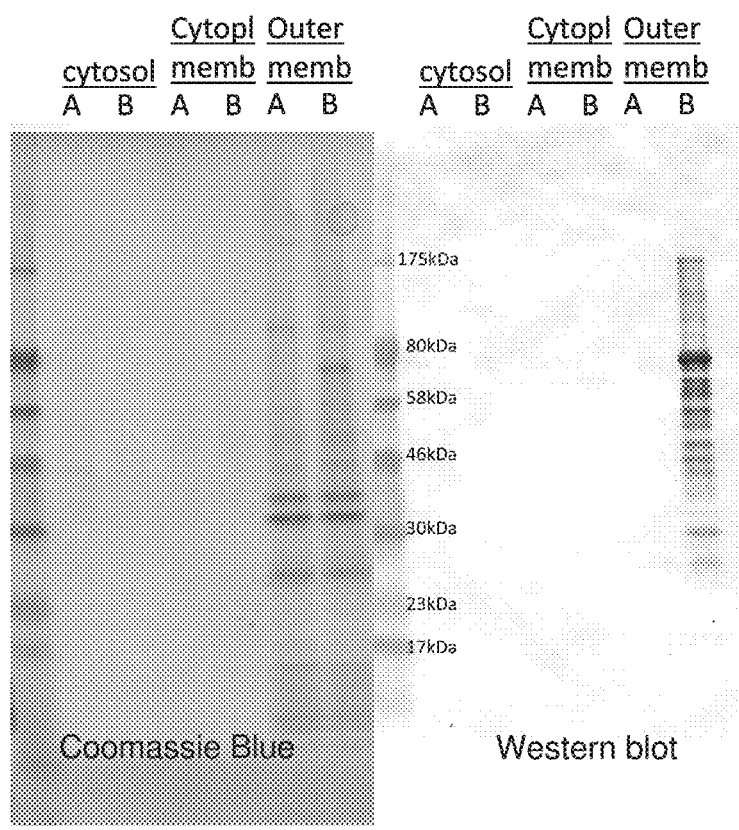

The EaeA-α3 fusion protein will be expressed from the araBAD promoter ($P_{bad}$), which responds, in a dose-dependent manner, to the concentration of arabinose added to the growth media. This will allow precise control over the density of α3 domains on the surface of bacterial cells. A diversification system, e.g. the L. pneumophila atd TR rt sequences (pDGR, FIG. 2), can be placed under control of the tightly regulated tetA promoter/operator on a multicopy plasmid. The expression of the atd TR rt sequences is induced by addition of anhydrotetracycline to the growth medium and will result in high frequency diversification of α3 VR sequences. Once diversification has been achieved, removal of inducer from the growth media will "lock" the system (α3-VR) into a stable state.

Diversification is first achieved by growing the surface display E. coli in the presence of arabinose to induce expression of the EaeA-α3 fusion protein, and anhydrotetracycline to induce diversification of α3-VR. Bacterial cells that display binding characteristics of interest can be enriched using standard methods such as Fluorescent Activated Cell Sorting (FACS) or magnetic bead separation techniques. Selected bacterial cells are amplified by growth in the presence of arabinose and the absence of anhydrotetracycline. Further enrichment steps can be included and additional rounds of optimization can be achieved by simply repeating the protocol. Importantly, α3 domains that bind to targets that are undesirable for NK or T-cell attack can be depleted from the diversified library by panning against, for example, normal tissues prior to selection for the desired binding properties. The selected α3 proteins can be cleaved from the bacterial cell surface by the addition of Factor Xa protease and then purified by affinity purification of the 6×His-tagged C-terminal domain for further characterization and use. This permits convenient biochemical and physical analyses of structure and function of the selected α3 domain. By fusing the isolated DNA encoding the desired, non-natural α3 domain to the portion of the MIC gene encoding an α1-α2 platform domain, the desired, non-natural α3 domain can then in each case be reintroduced into the rest of the soluble MIC protein via its linker or tether (amino acids 177-182) to create the desired passive NK cell vaccine with the specificity and sensitivity of the isolated α3 domain.

The selected genotype can be used to produce and isolate the non-natural or unnatural, soluble cognate MIC protein in bacteria, yeasts, insect or mammalian cells. The produced MICA can be purified to the required degree, formulated by available methods to stabilize it in vitro and in vivo, and administered parenterally or by other routes to humans or other mammals where it can diffuse to treat malignancies or viral diseases by promoting the targeted attack by the cellular components of the innate immunity system.

In some embodiments, a non-natural MIC molecule is formulated with a "pharmaceutically acceptable" excipient or carrier. Such a component is one that is suitable for use with humans or animals without undue adverse side effects. Non-limiting examples of adverse side effects include toxicity, irritation, and/or allergic response. The excipient or carrier is typically one that is commensurate with a reasonable benefit/risk ratio. In many embodiments, the carrier or excipient is suitable for topical or systemic administration. Non-limiting pharmaceutically carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Optionally, a composition comprising a non-natural MIC molecule of the disclosure may also be lyophilized or spray dried using means well known in the art. Subsequent reconstitution and use may be practiced as known in the field.

Pharmaceutical grade organic or inorganic carriers and/or diluents suitable for oral and topical use can be used to make up compositions comprising the therapeutically-active compounds. Stabilizing agents, wetting and emulsifying agents, salts for varying the osmotic pressure, or buffers for securing an adequate pH value may be included.

A non-natural MIC molecule is typically used in an amount or concentration that is "safe and effective", which refers to a quantity that is sufficient to produce a desired therapeutic response without undue adverse side effects like those described above. A non-natural MIC molecule may be biochemically modified to alter its pharmacokinetic properties in vivo. Well-known methods to increase half-life of circulating protein molecules are to chemically attach polyethylene glycol (PEG) to the basic structure or by genetic engineering to add polymers of natural amino acids such as glycine and serine to the N-terminus, C-terminus, or internally such as in the tether between α1-α2 and α3 domains, amino acids 179-182 of SEQ ID NOS: 1-13, without affecting binding functions of the MIC protein. A non-natural MIC molecule may be used in an amount or concentration that is "therapeutically effective", which refers to an amount effective to yield a desired therapeutic response, such as, but not limited to, an amount effective to bind target cells in order to recruit sufficient NK or T-cells to kill the target cells. The safe and effective amount or therapeutically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

EXAMPLES

As provided herein, two technologies both well-known to those of ordinary skill in the art, were used to physically attach the genotype of a MICA α3 domain to its (binding) phenotype so as to enable selection, screening, or panning in order to isolate the DNA encoding the desired phenotype. The first was bacterial surface display, wherein the α3 domain was displayed on the surface of a bacterium harboring the DNA encoding that α3 domain. The second was bacteriophage display of the α3 domain as a chimeric phage capsid protein, wherein the encoding DNA, the genotype, was within the phage genome. The ability to use the same α3 domain genotypes to make soluble, modified human MICA molecules with the binding phenotypes reflecting those of the displayed α3 domains is also demonstrated herein.

1. Display of MIC-α3 Domain Protein on the Surface of *E. coli*

In brief, the DNA encoding the α3 domain was fused to a portion of the *E. coli* eaeA (intimin) gene, and the resulting fusion protein was expressed on the surface of *E. coli* in such a manner that the α3 domain was oriented with its C-terminal portion distal to the bacterial surface.

Oligonucleotides AV1401 (SEQ ID NO: 15) and AV1402 (SEQ ID NO: 16) were kinased, annealed, and ligated into an aliquot of plasmid pET30a (Novagen) which had been digested with NdeI and NcoI to create pSW249, containing a pelB secretion signal sequence.

Plasmid pSW249 was digested with NcoI and BlpI and ligated together with kinased and annealed oligonucleotides AV1445 (SEQ ID NO: 17) and AV1446 (SEQ ID NO: 18) to create pSW263. This construct contained sequence encoding six histidine residues (SEQ ID NO:127) following the pelB sequence.

A human MICA cDNA comprising a portion of 5' untranslated sequence, signal sequence, and codons 1-276 of the mature coding sequence, followed by a stop codon, was amplified by PCR from human spleen first strand cDNA (acquired from Invitrogen) using primers AV1466 (SEQ ID NO: 19) and AV1448 (SEQ ID NO: 20).

The PCR fragment was digested with NheI and HindIII and ligated together with pCDNA5-FRT (Invitrogen) which had also been digested with NheI and HindIII to create pSW265. Three mutations the MICA coding region were corrected, G14W, A24T and E125K, by directed mutagenesis to create pSW271.

A portion of pSW271 was PCR amplified with primers AV1447 (SEQ ID NO: 21) and AV1448 (SEQ ID NO: 20). The PCR fragment consisted of a tev protease cleavage site, ENLYFQG (SEQ ID NO: 128), followed by codons 1-276 of human MICA. This PCR fragment was digested with XhoI and HindIII and ligated together with an aliquot of plasmid pSW263 which had also been digested with XhoI and HindIII to create plasmid pSW286.

The eaeA gene was amplified from *E. coli* EDL933 genomic DNA using AV1408 (SEQ ID NO: 22) and AV1409 (SEQ ID NO: 23) primers.

This PCR product was digested with BamHI and HindIII and ligated together with Bluescript-SK+ DNA (Stratagene) which had also been digested with BamHI and HindIII to create pSW284.

A portion of plasmid pSW284 was PCR amplified using primers AV1602 (SEQ ID NO: 24) and AV1603 (SEQ ID NO: 25). The PCR fragment was digested with NdeI and XhoI and ligated together with an aliquot of pSW286 which had also been digested with NdeI and XhoI to create pSW289.

A portion of pSW289 was PCR amplified with primers kk43 (SEQ ID NO: 26) and kk44 (SEQ ID NO: 27). The resulting PCR fragment containing a tev protease cleavage site, ENLYFQG (SEQ ID NO: 128), followed by sequence encoding residues 181 through 276 of MICA (note: the codon for P183 WAS changed from CCC to CCA to break up a run of 6 C's) was digested with XhoI and HindIII and ligated together with a ~7185 bp fragment which had been purified on an agarose gel from a digest of a separate aliquot of pSW289 digested with XhoI and HindIII to create pKK5. The 7185 bp fragment encoded EaeA 1-659 followed by GG then a factor Xa cleavage site, IEGR (SEQ ID NO: 129), then six His residues (SEQ ID NO: 127), then an XhoI site encoding LE of no function except to provide the XhoI site.

pKK5 was PCR amplified with primers kk52 (SEQ ID NO: 28) and kk45 (SEQ ID NO: 29). The PCR fragment was digested with NcoI and HindIII and ligated together with an aliquot of pBAD24 (from ATCC) which had been digested with NcoI and HindIII to create pKK29. The plasmid pKK29 was transformed according to the manufacturer's recommendations into the cloning strain, *E. coli* "NEB 10-beta" (catalog AV C3019H from New England BioLabs) and selected for resistance to 100 μg/ml carbenicillin.

Cytosolic proteins, inner membrane proteins, and outer membrane proteins of arabinose-induced and non-induced pKK29-transformed *E. coli* cells were each isolated and analyzed by SDS-PAGE. The SDS-PAGE gels were stained with Coomassie blue or western-blotted with antibody to human MICA protein.

Cells were grown in LB/Carb100 until $OD_{600}$ equaled 0.915. Aliquots of 10 mls of cells were added to each of two 50 ml conical tubes. One tube was induced with 0.002% arabinose; the other was left un-induced. Samples were incubated with shaking @ 37° C. for 1 hr.

Cells were then centrifuged for 10 min at 4000 rpm in an Eppendorf 5810R tabletop centrifuge. Supernatants were discarded and the cell pellets were gently resuspended in 6 ml FP buffer (0.1 M sodium phosphate buffer pH 7.0, 0.1 M KCl, 5 mM EDTA, 1 mM dithiothreitol, 1 mM phenylmethylsulfonyl fluoride) and transferred to 15 ml conical tubes. Cells were sonicated for 6×15 sec bursts using a Biologics Inc model 300 V/T ultrasonic homogenizer. Samples were incubated on ice between bursts. After sonication the tubes were centrifuged in the Eppendorf 5810R tabletop centrifuge at 4000 rpm for 5 minutes to remove any unbroken cells.

Supernatants were transferred to Beckman polycarbonate centrifuge tubes (catAV355631) and spun at 100,000×g for 1 hr at 4° C. in a Beckman L8-80M floor ultracentrifuge using a Type 60Ti rotor. The supernatants containing the cytosolic proteins were removed to new tubes and stored at 4° C.

The pellets of the cell membranes were resuspended in 2 mls of ME buffer (10 mM Tris-HCl pH 8.0, 35 mM $MgCl_2$, 1% Triton X-100). Samples shook gently for 2 hrs at 25° C. and then were re-centrifuged in the Beckman L8-80M floor ultracentrifuge using a Type 60Ti rotor at 100,000×g for 30 min at 4° C. Supernatants containing the cytoplasmic membrane Triton-soluble proteins were removed to new tubes and stored at 4° C. The final pellets containing the outer membrane proteins (Schnaitman, Calif. 1971. Solubilization of the Cytoplasmic Membrane of *Escherichia coli* by Triton X-100. J. Bacteriology 108: 545-552) were resuspended in 0.1 ml of water and also stored at 4° C. before being subjected to analyses by SDS-PAGE and stained by Coomassie Blue or western blotted using a goat polyclonal antibody against human MICA, FIG. 2.

For SDS-PAGE analyses samples were mixed with equal volumes of Novex Tris-Glycine SDS 2× sample buffer (Invitrogen AVLC2676) and electrophoresed on 4-20% Tris-Glycine Gradient Gel (Invitrogen AVEC60285BOX). For western blotting the electrophoresed sample lanes in the slab gel were transferred to a nitrocellulose membrane (Invitrogen Nitrocellulose Membrane Filter Paper Sandwich AVLC2001) using an Invitrogen XCell II Blot Module (AVE19051). The membrane filter was blocked overnight at 4° C. in 5% milk-Phosphate Buffered Saline, Tween-20 (PBST). Primary antibody (anti-human MICA antibody—R&D Systems AVAF1300) was used at 1:500 dilution in 5% milk-PBST. The resulting filter "blot" was incubated 2 hrs at 25° C. with gentle rocking The filter "blot" was subsequently washed for 20 min at 25° C. with PBST after which the secondary antibody (anti-goat IgG-HRP antibody—R&D Systems AVHAF017) was added at a dilution of 1:1000 in 5% milk-PBST. The filter "blot" was rocked for 2 hrs at 25° C. and then again was washed 20 min in PBST. The filter "blot" was developed with Novex HRP Chromogenic Substrate—TMB (Invitrogen AVWP20004).

To confirm bacterial surface display of the α3 domain by an independent method, fluorescent microscopy of intact, arabinose-induced and un-induced *E. coli* confirmed the staining of MICA α3 on the surface of intact bacteria from the induced culture only.

Figure 3:
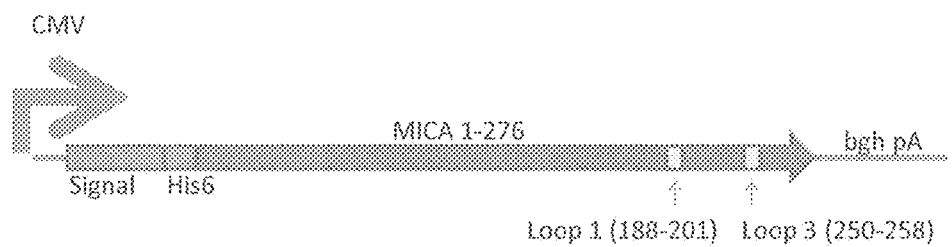
Figure 4:
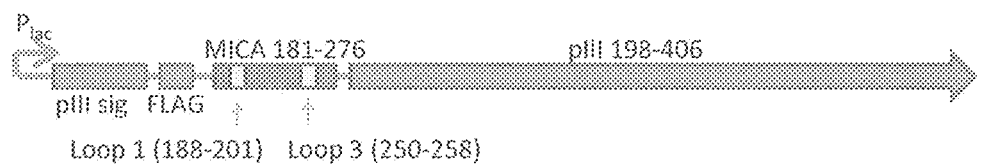

2. Generation of Soluble, Non-Natural, Human MIC Proteins With Internal Targeting Domains Human MICA is naturally glycosylated, although its unglycosylated form does bind its receptor, NKG2D, in vitro (Li et al., 2001). However, to be able to evaluate a human-like glycosylated form in vitro and eventually in vivo, we expressed MICA in cultured human cells. For expression, two common human alleles were inserted into the transient expression vector pcDNA5/FRT, which has a human CMV promoter and a bovine growth hormone (bgh) polyadenylation signal, FIG. 3.

Working Plasmid Constructions

The secretion signal sequence and codons 1-276 of mature HUMMHCREP (Human MHC class I-related protein mRNA) were obtained by amplifying with a Polymerase Chain Reaction (PCR) the appropriate DNA sequence from human spleen first-strand cDNA (available from Life Technologies/Invitrogen) using primers AV1466 (SEQ ID NO: 30) and AV1448 (SEQ ID NO: 31).

The amplified DNA product was digested with NheI and HindIII restriction enzymes, and the resulting product was ligated into NheI/HindIII-digested pCDNA5/FRT (Invitrogen), to create pSW265.

The DNA of the inserted PCR product of pSW265 was sequenced and verified to include an NheI site followed by 26 bases of the 5' untranslated (UT) sequence, followed by secretion signal sequence and codons 1-276 of mature HUMMH-CREP, followed by a termination codon, followed by a HindIII site. Where the coding sequence deviated from the intended sequence such that it would result in an amino acid difference if translated, the codons were changed by site-directed mutagenesis (using New England BioLabs Phusion® site-directed mutagenesis kit and appropriate primers) so that the amino acid sequence matched the relevant portion (amino acids 1-276) of the sequence described as SEQ ID NO: 13.

The corrected plasmid was designated pSW271 and contained the corrected DNA sequence encoding 26 bases of the 5'UT sequence, followed by secretion signal sequence and codons 1-276 of mature HUMMHCREP, followed by a termination codon, SEQ ID NO:14

Primers AV1490 (SEQ ID NO: 32) and AV1489 (SEQ ID NO: 33) and pSW271 were used to generate a PCR product which was subsequently digested with BamHI and BsmBI and ligated to ~5259 bp BamHI/BsmBI fragment from pSW271. The resulting construct pSW275 lacks a BsmBI site.

Using New England BioLabs Phusion® site-directed mutagenesis kit and primers AV1493 (SEQ ID NO: 34) and AV1494 (SEQ ID NO: 35), two BsmBI sites were inserted in the MICA coding region of pSW275, creating pSW276.

Plasmid pSW267 is the same as pSW271 except MICA codon 125 is GAG (Glu) instead of AAG (Lys). It was derived from pSW265 by site-directed mutagenesis (using New England BioLabs Phusion kit with primers AV1478 (SEQ ID NO:39) and AV1479 (SEQ ID NO:40). This mutagenesis changed MICA codon 14 from GGG (Gly) to TGG (Trp) and codon 24 from GCT (Ala) to ACT (Thr).

Plasmid pSW273 was made from pSW267 by site-directed mutagenesis using primers AV1486 (SEQ ID NO:41) and AV1487 (SEQ ID NO:42). pSW273 contains six histidine codons between the signal peptide and residue 1 of the mature peptide.

Plasmid pKK33 is identical to plasmid pSW273 except a BsmBI site has been deleted from the partial hph (hygromycin resistance) gene. A PCR fragment was obtained from plasmid pSW273 by amplifying with primers AV1490 (SEQ ID NO:32) and 1489 (SEQ ID NO:33). This ~727 bp fragment was digested with BamHI and BsmBI and was ligated together with the ~5277 bp BamHI/BsmBI-digested fragment from pSW273. This resulted in the removal of the BsmBI site and the creation of pKK34.

The following describes constructs derived from pKK34 to insert binding sequences into loop 1 of MICA α3 domain.

The following loop 1 constructs were generated by insertion of the indicated heterologous peptide "insert" between T189 and V200 of MICA and replacing the residues at positions 190-199 with the indicated insert.

To create pKK36, which has a sequence coding for SRGDHPRTQ (SEQ ID NO:43; referred to as loop 3.1) inserted between T189 and V200 of MICA, phosphorylated oligonucleotides AV1830 (top strand) (SEQ ID NO:44) and AV1831 (bottom strand) (SEQ ID NO:45) were ligated into BsmBI-digested pKK34.

To create pKK37, which has a sequence coding for RTSRGDHPRTQ (SEQ ID NO:46; referred to as loop 3.2) inserted between T189 and V200 of MICA, phosphorylated oligonucleotides AV1832 (top strand) (SEQ ID NO:47) and AV1833 (bottom strand) (SEQ ID NO:48) were ligated into BsmBI-digested pKK34.

To create pKK38, which has a sequence coding for RVPRGDSDLT (SEQ ID NO:49; referred to as loop 3.3) inserted between T189 and V200 of MICA, phosphorylated oligonucleotides AV1834 (top strand) (SEQ ID NO:50) and AV1835 (bottom strand) (SEQ ID NO:51) were ligated into BsmBI-digested pKK34.

To create pKK39, which has a sequence coding for RSARGDSDHR (SEQ ID NO:52; referred to as loop 3.4) inserted between T189 and V200 of MICA, phosphorylated oligonucleotides AV1836 (top strand) (SEQ ID NO:53) and AV1837 (bottom strand) (SEQ ID NO:54) were ligated into BsmBI-digested pKK34.

To create pKK40, which has a sequence coding for VTRGDTFTQS (SEQ ID NO:55; referred to as loop 5.1) inserted between T189 and V200 of MICA, phosphorylated oligonucleotides AV1838 (top strand) (SEQ ID NO:56) and AV1839 (bottom strand) (SEQ ID NO:57) were ligated into BsmBI-digested pKK34.

To create pKK41, which has a sequence coding for RGDT-FTQS (SEQ ID NO:58; referred to as loop 5.2) inserted between T189 and V200 of MICA, phosphorylated oligonucleotides AV1840 (top strand) (SEQ ID NO:59) and AV1841 (bottom strand) (SEQ ID NO:60) were ligated into BsmBI-digested pKK34.

To create pKK42, which has a sequence coding for HLARGDDLTY (SEQ ID NO:61; referred to as loop 5.3) inserted between T189 and V200 of MICA, phosphorylated oligonucleotides AV1842 (top strand) (SEQ ID NO:62) and AV1843 (bottom strand) (SEQ ID NO:63) were ligated into BsmBI-digested pKK34.

To create pKK44, which has a sequence coding for SGGSGGGSTSRGDHPRTQSGGSGGG (SEQ ID NO:64; referred to as extended loop 3.2sp) inserted between T189 and V200 of MICA, phosphorylated oligonucleotides AV1854 (top strand) (SEQ ID NO:65) and AV1855 (bottom strand) (SEQ ID NO:66) were ligated into BsmBI-digested pKK34.

To create pKK45, which has a sequence coding for SGGSGGGSRVPRGDSDLTSGGSGGG (SEQ ID NO:67; referred to as extended loop 3.3sp) inserted between T189 and V200 of MICA, phosphorylated oligonucleotides AV1856 (top strand) (SEQ ID NO:68) and AV1857 (bottom strand) (SEQ ID NO:69) were ligated into BsmBI-digested pKK34.

To create pKK46, which has a sequence coding for SGGSGGGSVTRGDTFTQSSGGSGGG (SEQ ID NO:70; referred to as extended loop 5.1sp) inserted between T189 and V200 of MICA, phosphorylated oligonucleotides AV1858 (top strand) (SEQ ID NO:71) and AV1859 (bottom strand) (SEQ ID NO:72) were ligated into BsmBI-digested pKK34.

To create pKK47, which has a sequence coding for SGGSGGGSHLARGDDLTYSGGSGGG (SEQ ID NO:73; referred to as extended loop 5.3sp) inserted between T189 and V200 of MICA, phosphorylated oligonucleotides AV1860 (top strand) (SEQ ID NO:74) and AV1861 (bottom strand) (SEQ ID NO:75) were ligated into BsmBI-digested pKK34.

The following describes constructs to insert binding sequences into loop 3.

The following loop 3 constructs were generated by insertion of the indicated heterologous peptide "insert" between MICA residues Isoleucine 249 and Cysteine 259 and replacing the residues at positions 250-258 with the indicated insert.

The plasmid pSW276 was digested with BsmBI and ligated to kinased and annealed oligonucleotides AV1826 (SEQ ID NO: 36) and AV1827 (SEQ ID NO: 37) to create pKK35. This plasmid contained a sequence encoding SGGSGGGSHHHHHHHHHHSGGSGGG (SEQ ID NO: 38) between MICA residues Isoleucine 249 and Cysteine 259 and replacing the residues at positions 250-258.

To create pKK48, which has a sequence coding for SGGSGGGSTSRGDHPRTQSGGSGGG (SEQ ID NO:76; referred to as extended loop 3.2sp) inserted between I249 and C259 of MICA, phosphorylated oligonucleotides AV1864 (top strand) (SEQ ID NO:77) and AV1865 (bottom strand) (SEQ ID NO:78) were ligated into BsmBI-digested pSW276.

To create pKK49, which has a sequence coding for SGGSGGGSRVPRGDSDLTSGGSGGG (SEQ ID NO:79; referred to as extended loop 3.3sp) inserted between I249 and C259 of MICA, phosphorylated oligonucleotides AV1866 (top strand) (SEQ ID NO:80) and AV1867 (bottom strand) (SEQ ID NO:81) were ligated into BsmBI-digested pSW276.

To create pKK50, which has a sequence coding for SGGSGGGSVTRGDTFTQSSGGSGGG (SEQ ID NO:82; referred to as extended loop 5.1sp) inserted between I249 and C259 of MICA, phosphorylated oligonucleotides AV1868 (top strand) SEQ ID NO:83) and AV1869 (bottom strand) (SEQ ID NO:84) were ligated into BsmBI-digested pSW276.

To create pKK51, which has a sequence coding for SGGSGGGSHLARGDDLTYSGGSGGG (SEQ ID NO:85; referred to as extended loop 5.3sp) inserted between I249 and C259 of MICA, phosphorylated oligonucleotides AV1870 (top strand) (SEQ ID NO:86) and AV1871 (bottom strand) (SEQ ID NO:87) were ligated into BsmBI-digested pSW276.

The following describes constructs to insert binding sequences into a "tight" loop 1.

The following "tight" (T) loop 1 constructs were generated by insertion of the indicated heterologous peptide "insert" between N187 and C202 of MICA, that is, residues 188-201 of MICA were replaced with the indicated insert.

The plasmid pKK34 was mutagenized with primers AV1873 (SEQ ID NO:88) and AV1872 (SEQ ID NO:89) to create pSW324, which contains convenient BsmBI sites suitable for cloning inserts between N187 and C202 of MICA.

To create pKK52, which has a sequence coding for TSRGDHPRTQ (SEQ ID NO:90; referred to as tight T-3.1) inserted between N187 and C202 of MICA, phosphorylated oligonucleotides AV1874 (top strand) (SEQ ID NO:91) and AV1875 (bottom strand) (SEQ ID NO:92) were ligated into BsmBI-digested pSW324.

To create pKK53, which has a sequence coding for GSRGDSLIMH (SEQ ID NO:93; referred to as tight T-3.5) inserted between N187 and C202 of MICA, phosphorylated oligonucleotides AV1876 (top strand) (SEQ ID NO:94) and AV1877 (bottom strand) (SEQ ID NO:95) were ligated into BsmBI-digested pSW324.

To create pKK54, which has a sequence coding for RVPRGDSDLT (SEQ ID NO:96; referred to as tight T-3.3) inserted between N187 and C202 of MICA, phosphorylated oligonucleotides AV1878 (top strand) (SEQ ID NO:97) and AV1879 (bottom strand) (SEQ ID NO:98) were ligated into BsmBI-digested pSW324.

To create pKK55, which has a sequence coding for VTRGDTFTQS (SEQ ID NO:99; referred to as tight T-5.1) inserted between N187 and C202 of MICA, phosphorylated oligonucleotides AV1880 (top strand) (SEQ ID NO:100) and AV1881 (bottom strand) (SEQ ID NO:101) were ligated into BsmBI-digested pSW324.

To create pKK56, which has a sequence coding for HLARGDDLTY (SEQ ID NO:102; referred to as tight T-5.3) inserted between N187 and C202 of MICA, phosphorylated oligonucleotides AV1882 (top strand) (SEQ ID NO:103) and AV1883 (bottom strand) (SEQ ID NO:104) were ligated into BsmBI-digested pSW324.

To create pKK84, which has a sequence coding for YQSWRYSQ (SEQ ID NO:105; loop 1 from tendamistat, referred to as tight T-AMY) inserted between N187 and C202 of MICA, phosphorylated oligonucleotides AV 1906 (top strand) (SEQ ID NO:106) and AV 1907 (bottom strand)(SEQ ID NO:107) were ligated into BsmBI-digested pSW324.

The following describes constructs to insert binding sequences into both loop 1 and loop 3 of the same soluble MICA molecules.

To create constructs encoding soluble MICA molecules with binding sequences inserted into both loop 1 and loop 2, we created pKK115. Vector pKK115 encodes extended 5.1sp (SEQ ID NO:82) in loop 1 and convenient BsmBI sites suitable for cloning other sequences into loop 3. Vector pKK115 was created by site-directed mutagenesis of pKK46 with primers AV1493 (SEQ ID NO:108) and AV1494 (SEQ ID NO:109).

To create pKK128, which has extended 5.1sp in loop 1 and a sequence coding for SGGSGGGSTSRGDH-PRTQSGGSGGG (SEQ ID NO:76) referred to as extended loop 3.2sp) inserted between I249 and C259 of MICA, phosphorylated oligonucleotides AV1864 (top strand) (SEQ ID NO:77) and AV1865 (bottom strand) (SEQ ID NO:78) were ligated into BsmBI-digested pKK115.

To create pKK129, which has extended 5.1sp in loop 1 and a sequence coding for SGGSGGGSVTRGDT-FTQSSGGSGGG (SEQ ID NO:82; referred to as extended loop 5.1sp) inserted between I249 and C259 of MICA, phosphorylated oligonucleotides AV1868 (top strand) (SEQ ID NO:83) and AV1869 (bottom strand) (SEQ ID NO:84) were ligated into BsmBI-digested pKK115.

To create pKK130, which has extended 5.1sp in loop 1 and a sequence coding for SGGSGGGSHLARGDDL-TYSGGSGGG (SEQ ID NO:85; referred to as extended loop 5.3sp) inserted between I249 and C259 of MICA, phosphorylated oligonucleotides AV1870 (top strand) (SEQ ID NO:86) and AV1871 (bottom strand) (SEQ ID NO:87) were ligated into BsmBI-digested pKK115.

To create pKK131, which has extended 5.1sp in loop 1 and a sequence coding for SGGSGGGSVTRGDT-FTQSSGGSGGG (SEQ ID NO:82) referred to as non-homologous extended loop 5.1spNH) inserted between I249 and C259 of MICA, phosphorylated oligonucleotides AV1908 (top strand) (SEQ ID NO: 110) and AV1909 (bottom strand) (SEQ ID NO:111) were ligated into BsmBI-digested pKK115.

The following describes the cultured human cell expression of the above created constructs encoding soluble MICA molecules with internal binding inserts and the ELISA-based analyses of their target binding.

For plasmid constructs pKK35-42, pKK44-56 and pKK128-131, 90% confluent cultures of 293T cells (ATCC) in 10 cm tissue culture dishes were transfected with 10 μg of each plasmid DNA using Fugene HD transfection reagent (Roche Applied Science). After 3 days the culture medium of each culture was collected and cleared of floating cells by centrifugation at 4000 rpm in an Eppendorf 5810R tabletop centrifuge. The recovered ~9.5 ml of each sample was concentrated using a Pierce concentrator 7 ml/9K (catalog AV89884A) spin tube. The concentrators were pre-rinsed with phosphate buffered saline (PBS). Each sample was added to the concentrator and then centrifuged for 30 min at 4000 rpm in the Eppendorf 5810R tabletop centrifuge. Each sample was washed and concentrated 3 times with 6 ml PBS—each time spinning 4000 rpm 30 min in the Eppendorf 5810R tabletop centrifuge. The concentration of soluble MICA in each resulting sample solution was estimated by an ELISA for soluble MICA. The capture agent was mouse anti-human MICA (R&D Systems part 841612), and the detection antibody was biotinylated goat anti-human MICA (R&D Systems part 841613) that was developed with Streptavidin-HRP and Ultra TMB.

The ability of the soluble MICA molecules in each of the concentrated supernatants to bind target molecules was assayed by an ELISA using the intended target proteins, integrin αVβ3 or αVβ5, as capture agents on the ELISA plate. After the respective integrins were adhered to the bottoms of the wells of the ELISA plate, the wells were washed and blocked, as well known in the field. Each sample (100 μl) of soluble MICA produced and secreted by 293T cells was added to wells containing αVβ3 or αVβ5, incubated and washed. The soluble MICA molecules captured by the integrins were detected by HRP-conjugated antibody to human MICA developed with Ultra TMB-ELISA substrate and the optical densities read. The quantity of soluble MICA in each sample was determined by the MICA-specific ELISA. The signals from the bound soluble MICA molecules (per ng of total MICA) to the specific integrins are shown. The ELISA signal from a non-binding, negative control MICA (generated by pSW273) was subtracted from each integrin binding signal. The results of the MICA products with single peptides inserts generated from pKK35-42 and pKK44-56 along with controls are shown in Table 1. The amino acid sequences and SEQ ID NOs of their specific inserts are tabulated in Table 2. Soluble MICA molecules with binding peptides inserted by genetic engineering into only one of their loops bound to the integrin targets.

TABLE 1

Integrin binding ELISA data from single inserts in soluble MICA

| plasmid name | insert loop 1 | insert loop 3 | MICA (pg/well) | αvβ3 signal | αvβ5 signal | αvβ3 signal/ng | αvβ5 signal/ng |
|---|---|---|---|---|---|---|---|
| pKK35 | wild type | His10sp | 170.00 | 0.419 | 0.392 | 2.46 | 2.31 |
| pKK36 | 3.1 | wild type | 29.00 | 0.550 | 0.526 | 18.97 | 18.14 |
| pKK37 | 3.2 | wild type | 34.70 | 0.777 | 0.779 | 22.39 | 22.45 |
| pKK38 | 3.3 | wild type | 9.48 | 0.291 | 0.291 | 30.70 | 30.70 |
| pKK39 | 3.4 | wild type | 26.79 | 0.482 | 0.528 | 17.99 | 19.71 |
| pKK40 | 5.1 | wild type | 24.87 | 0.485 | 0.675 | 19.50 | 27.14 |
| pKK41 | 5.2 | wild type | 29.08 | 0.516 | 0.650 | 17.74 | 22.35 |
| pKK42 | 5.3 | wild type | 24.77 | 0.526 | 0.565 | 21.24 | 22.81 |
| pKK44 | 3.2sp | wild type | 45.94 | 0.410 | 0.460 | 8.92 | 10.01 |
| pKK45 | 3.3sp | wild type | 41.32 | 0.393 | 0.410 | 9.51 | 9.92 |
| pKK46 | 5.1sp | wild type | 41.75 | 0.384 | 1.065 | 9.20 | 25.51 |
| pKK47 | 5.3sp | wild type | 29.44 | 0.294 | 0.276 | 9.99 | 9.38 |
| pKK48 | wild type | 3.2sp | 78.65 | 0.478 | 0.604 | 6.08 | 7.68 |
| pKK49 | wild type | 3.3sp | 86.75 | 0.508 | 0.478 | 5.86 | 5.51 |
| pKK50 | wild type | 5.1sp | 93.26 | 0.546 | 0.721 | 5.85 | 7.73 |
| pKK51 | wild type | 5.3sp | 96.34 | 0.694 | 1.048 | 7.20 | 10.88 |
| pKK52 | T-3.1 | wild type | 38.61 | 0.391 | 0.485 | 10.13 | 12.56 |
| pKK53 | T-3.5 | wild type | 35.16 | 0.659 | 0.800 | 18.74 | 22.75 |
| pKK54 | T-3.3 | wild type | 9.06 | 0.177 | 0.175 | 19.54 | 19.32 |
| pKK55 | T-5.1 | wild type | 33.83 | 0.475 | 0.588 | 14.04 | 17.38 |
| pKK56 | T-5.3 | wild type | 28.86 | 0.473 | 0.528 | 16.39 | 18.30 |

TABLE 2

Correlations of the plasmids expressed in 293 cells and the phage plasmids, their trivial names, the amino acid sequences inserted into loop 1, loop 3 or both loop 1 and loop 3, and the corresponding SEQ ID NOs of the inserts.

| plasmids | | | | | | |
|---|---|---|---|---|---|---|
| 293 cells | M13 phage | trivial name | Loop 1 | SEQ ID NO: | Loop 3 | SEQ ID NO: |
| SW273 | KK106 | WT | RSEASEGNIT | 13 (residues 190-199) | ICQGEEQRFT | 13 (residues 250-258) |
| KK35 | KK91 | 3-His10 | | | SGGSGGGSHHHHH HHHHHSGGSGGG | 38 |
| KK36 | KK92 | 1-3.1 | SRGDHPRTQ | 43 | | |
| KK37 | KK93 | 1-3.2 | RTSRGDHPRTQ | 46 | | |
| KK38 | KK94 | 1-3.3 | RVPRGDSDLT | 49 | | |
| KK39 | KK95 | 1-3.4 | RSARGDSDHR | 52 | | |
| KK40 | KK96 | 1-5.1 | VTRGDTFTQS | 55 | | |
| KK41 | KK97 | 1-5.2 | RGDTFTQS | 58 | | |
| KK42 | KK98 | 1-5.3 | HLARGDDLTY | 61 | | |
| KK44 | KK100 | 1-3.2sp | SGGSGGGSTSRGDHPRTQSGGSGGG | 64 | | |
| KK45 | KK101 | 1-3.3sp | SGGSGGGSRVPRGDSDLTSGGSGGG | 67 | | |
| KK46 | KK102 | 1-5.1sp | SGGSGGGSVTRGDTFTQSSGGSGGG | 70 | | |
| KK47 | KK103 | 1-5.3sp | SGGSGGGSHLARGDDLTYSGGSGGG | 73 | | |
| KK48 | KK104 | 3-3.2sp | | | SGGSGGGSTSRGD HPRTQSGGSGGG | 76 |
| KK49 | KK105 | 3-3.3sp | | | SGGSGGGSRVPRG DSDLTSGGSGGG | 79 |
| KK50 | | 3-5.1sp | | | SGGSGGGSVTRGD TFTQSSGGSGGG | 82 |
| KK51 | | 3-5.3sp | | | SGGSGGGSHLARG DDLTYSGGSGGG | 85 |
| KK52 | KK107 | 1-1-3.1 | TSRGDHPRTQ | 90 | | |
| KK53 | KK108 | 1-T-3.5 | GSRGDSLIMH | 93 | | |
| KK54 | KK109 | 1-1-3.3 | RVPRGDSDLT | 96 | | |
| KK55 | KK110 | 1-T-5.1 | VTRGDTFTQS | 99 | | |
| KK56 | K111 | 1-T-5.3 | HLARGDDLTY | 102 | | |
| KK84 | KK112 | 1-T-AMY | YQSWRYSQ | 105 | | |
| KK128 | KK136 | 1-5.1sp/3-3.2sp | SGGSGGGSVTRGDTFTQSSGGSGGG | 70 | SGGSGGGSTSRGD HPRTQSGGSGGG | 76 |
| KK129 | KK137 | 1-5.1sp/3-5.1sp | SGGSGGGSVTRGDTFTQSSGGSGGG | 70 | SGGSGGGSVTRGD TFTQSSGGSGGG | 82 |
| KK130 | KK138 | 1-5.1sp/3-5.3sp | SGGSGGGSVTRGDTFTQSSGGSGGG | 70 | SGGSGGGSHLARG DDLTYSGGSGGG | 85 |
| KK131 | KK139 | 1-5.1sp/3-5.1spNH | SGGSGGGSVTRGDTFTQSSGGSGGG | 70 | SGGSGGGSVTRGD TFTQSSGGSGGG | 82 |

The results of the MICA products with binding peptides inserted into more than one loop generated from pKK128-131 along with controls are shown in Table 3. ELISA assays of the integrin target-binding of soluble MICA molecules generated from pKK128-131 were performed as follows. After the respective integrins were adhered to the bottoms of the wells of the ELISA plate, the wells were washed and blocked. Each sample (100 μl) of culture supernatant was added to wells containing αVβ3 or αVβ5, incubated and washed. The soluble MICA molecules captured by the integrins were detected by HRP-conjugated antibody to human MICA developed with Ultra TMB-ELISA substrate and the optical densities read. The quantity of soluble MICA in each sample was determined by the MICA-specific ELISA. The signal of soluble MICA molecules with more than 1 insert bound to the specific integrins (per ng of total MICA) are shown, Table 3. The amino acid sequences and SEQ ID NOs of their specific inserts are tabulated in Table 2. Those soluble MICA molecules with binding peptides inserted into more than 1 internal loop exhibited greater binding than those with only a single internal binding peptide, indicating the avidity effect of more than 1 binding motif per molecule. Furthermore, the specificity of a soluble MICA molecule for its intended target, for example αVβ5, was enhanced over the closely related target, αVβ3, when the soluble MICA molecule had more than one αVβ5-specific, internal binding peptide per MICA molecule. Such increased binding and specificity of binding were expected of a MICA molecule exhibiting avidity for its target. Thus, bivalent MICA binders were created, both duplicate binders and different binders, enabling the generation bi-specific MICA molecules and MICA molecules with avidity exceeding affinity for its target.

The following describes the constructions, expression, and assays of the M13 phages displaying MICA α3 domains with different binding peptides in loop 1, loop 3 or in both loop 1 and loop 3.

The M13 phage M13KE (obtained from New England BioLabs) was used as template in a PCR amplification reaction with primers AV1887 (SEQ ID NO:112) and AV1888 (SEQ ID NO:113).

The PCR product, consisting of a C-terminal portion of M13KE gene III, was digested with EcoRI and HindIII and ligated together with EcoRI/HindIII-digested M13 phage vector M13mp18 (GenBank X02513) to create phage vector pSW326.

Phage vector pKK59 was created by inserting the synthesized sequence TEND (SEQ ID NO:114), digested with EcoRI and AvrII, into EcoRI/AvrII-digested pSW326.

Phage vector pKK60 was created by inserting the synthesized sequence TEND-3A (SEQ ID NO:115), digested with EcoRI and AvrII, into EcoRI/AvrII-digested pSW326.

Phage vector pKK61 was created by inserting the synthesized sequence TEND-3B (SEQ ID NO:116), digested with EcoRI and AvrII, into EcoRI/AvrII-digested pSW326.

Phage vector pKK63 was created by inserting the synthesized sequence TEND-5A (SEQ ID NO:117), digested with EcoRI and AvrII, into EcoRI/AvrII-digested pSW326.

Phage vector pKK64 was created by inserting the synthesized sequence TEND-5B (SEQ ID NO:118), digested with EcoRI and AvrII, into EcoRI/AvrII-digested pSW326.

Phage vector pKK65 was created by inserting the synthesized sequence TEND-His8 (SEQ ID NO:119; His8 is SEQ ID NO:130), digested with EcoRI and AvrII, into EcoRI/AvrII-digested pSW326.

TABLE 3

Integrin binding ELISA data from double inserts in soluble MICA

| plasmid name | insert loop 1 | insert loop 3 | MICA (pg/well) | αvβ3 signal | αvβ5 signal | αvβ3 signal/ng | αvβ5 signal/ng |
|---|---|---|---|---|---|---|---|
| pSW273 | wild type | wild type | 14.7 | 0.099 | 0.100 | 6.73 | 6.80 |
| pKK46 | 5.1sp | wild type | 49.6 | 0.467 | 0.660 | 9.42 | 13.31 |
| pKK128 | 5.1sp | 3.2sp | 35.4 | 0.811 | 1.001 | 22.91 | 28.28 |
| pKK129 | 5.1sp | 5.1sp | 33.9 | 0.787 | 1.008 | 23.22 | 29.73 |
| pKK130 | 5.1sp | 5.2sp | 30.9 | 0.606 | 0.832 | 19.61 | 26.93 |
| pKK131 | 5.1sp | 5.1sp.nh | 30.7 | 0.685 | 1.071 | 22.31 | 34.89 |

3. Display of MICA-α3 Domain Protein on M13 Phage

To develop a system for the isolation of new genes encoding engineered MICA molecules with desired target binding phenotypes, the DNA encoding α3 domain amino acids 181-276 was fused to capsid gene III of M13 phage (M13mp18; Smith vector type "33") at codon position 198, FIG. 4, and generated without helper phage M13 phages with mixed wild type (wt) and α3-pIII chimeric capsids (Bass et al., 1990). Protein-stained SDS-PAGE analysis of PEG-purified phage preparations from *E. coli* confirmed the presence of both the fusion and wt pIII proteins in the population (data not shown).

Tendamistat is a bacterial protein with a 3-dimensional structure resembling that of the α3 domain of MICA (Pflugrath et al., 1986). Random peptides have been inserted into Tendamistat and selected by M13 phage display for binding to human integrins (McConnell and Hoess, 1995; Li et al., 2003). Tendamistat fused to pIII of M13 as positive controls for the ELISA assay. In parallel it was determined herein whether some of the same decapeptides inserted into loop 1 or into 3 of the MICA α3 domain could similarly direct M13 phage displaying the α3 domain fused to capsid pIII to bind integrins in the ELISA format.

To create phage vector pKK106, a ~320 bp fragment was amplified by PCR from pKK29 using primers AV1897 (SEQ ID NO:120) and AV1898 (SEQ ID NO:121). This fragment representing the wild type MICA α3 sequence (SEQ ID NOs: 1-6, 13), was then digested with EcoRI and BsmBI and ligated together with the ~7911 bp MfeI/AvrII-digested fragment of pKK59.

To create phage vector pKK91, a ~356 bp fragment was amplified by PCR from pKK35 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK92, a ~305 bp fragment was amplified by PCR from pKK36 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK93, a ~311 bp fragment was amplified by PCR from pKK37 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK94, a ~308 bp fragment was amplified by PCR from pKK38 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK95, a ~308 bp fragment was amplified by PCR from pKK39 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK96, a ~308 bp fragment was amplified by PCR from pKK40 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK97, a ~302 bp fragment was amplified by PCR from pKK41 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK98, a ~308 bp fragment was amplified by PCR from pKK42 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK100, a ~353 bp fragment was amplified by PCR from pKK44 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK101, a ~353 bp fragment was amplified by PCR from pKK45 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK102, a ~353 bp fragment was amplified by PCR from pKK46 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK103, a ~353 bp fragment was amplified by PCR from pKK47 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK104, a ~356 bp fragment was amplified by PCR from pKK48 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK105, a ~356 bp fragment was amplified by PCR from pKK49 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK107, a ~344 bp fragment was amplified by PCR from pKK52 using primers KK69 (SEQ ID NO:122) and AV1898 (SEQ ID NO:121). This fragment was then digested with EcoRI and BsmBI and ligated together with the ~7911 bp MfeI/AvrII-digested fragment of pKK59.

To create phage vector pKK108, a ~284 bp fragment was amplified by PCR from pKK53 using primers KK70 (SEQ ID NO:123) and AV1898 SEQ ID NO:121). This fragment was then digested with EcoRI and BsmBI and ligated together with the ~7911 bp MfeI/AvrII-digested fragment of pKK59.

To create phage vector pKK109, a ~284 bp fragment was amplified by PCR from pKK54 using primers KK71 (SEQ ID NO:124) and AV1898 (SEQ ID NO:121). This fragment was then digested with EcoRI and BsmBI and ligated together with the ~7911 bp MfeI/AvrII-digested fragment of pKK59.

To create phage vector pKK110, a ~284 bp fragment was amplified by PCR from pKK55 using primers KK72 (SEQ ID NO:125) and AV1898 (SEQ ID NO:121). This fragment was then digested with EcoRI and BsmBI and ligated together with the ~7911 bp MfeI/AvrII-digested fragment of pKK59.

To create phage vector pKK111, a ~284 bp fragment was amplified by PCR from pKK56 using primers KK73 (SEQ ID NO:126) and AV1898 (SEQ ID NO:121). This fragment was then digested with EcoRI and BsmBI and ligated together with the ~7911 bp MfeI/AvrII-digested fragment of pKK59.

To create phage vector pKK112, a ~278 bp fragment was amplified by PCR from pKK84 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK136, a ~413 bp fragment was amplified by PCR from pKK128 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK137, a ~413 bp fragment was amplified by PCR from pKK129 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK138, a ~413 bp fragment was amplified by PCR from pKK130 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

To create phage vector pKK139, a ~413 bp fragment was amplified by PCR from pKK131 using primers AV1897 (SEQ ID NO:120) and AV1898 (SEQ ID NO:121). This fragment was then digested with EcoRI and BsmBI and ligated together with the ~7911 bp MfeI/AvrII-digested fragment of pKK59.

The phage vectors were independently transformed into NEBαF'tet competent *E. coli* cells. Phages produced by the transformed cells were tittered and their concentrations adjusted by dilution to $10^{13}$ per ml. The ability of the soluble MICA molecules in each of the phage preparations was assayed by an ELISA using the intended target proteins, integrin αVβ3 or αVβ5, as capture agents on the ELISA plate. After the respective integrins were adhered to the bottoms of the wells of the ELISA plate, the wells were washed and blocked, as well known in the field. Each sample (100 μl) of phage preparation was added to wells containing αVβ3 or αVβ5, incubated and washed. The phages captured by the integrins were detected by HRP-conjugated antibody to the M13 phage coat developed with Ultra TMB-ELISA substrate and the optical densities read. The M13 phages titers ranged from $8\times10^{12}$ to $1.1\times10^{13}$/ml. The results of the phages displaying α3 domains with single peptides inserts generated from pKK91-98 and 100-112 are shown in Table 4. The amino acid sequences and SEQ ID NOs of their specific inserts are tabulated in Table 2. Phages displaying α3 domains with binding peptides inserted by genetic engineering into only one of their loops and fused to pIII capsid protein bind to integrin targets.

TABLE 4

Integrin binding ELISA data from single inserts in MICA α3-PIII bacteriophage display

| phage name | insert loop 1 | insert loop 3 | αvβ3 signal | αvβ5 signal |
|---|---|---|---|---|
| pKK106 | wild type | wild type | 0.000 | 0.000 |
| pKK91 | wild type | His10sp | 0.303 | 0.078 |
| pKK92 | 3.1 | wild type | 0.858 | 1.318 |
| pKK93 | 3.2 | wild type | 0.284 | 0.291 |
| pKK94 | 3.3 | wild type | 1.066 | 2.841 |
| pKK95 | 3.4 | wild type | 0.345 | 0.232 |
| pKK96 | 5.1 | wild type | 1.642 | 2.418 |
| pKK97 | 5.2 | wild type | 1.551 | 2.592 |
| pKK98 | 5.3 | wild type | 1.217 | 1.480 |
| pKK100 | 3.2sp | wild type | 0.201 | 0.186 |
| pKK101 | 3.3sp | wild type | 1.492 | 1.231 |
| pKK102 | 5.1sp | wild type | 1.016 | 0.771 |
| pKK103 | 5.3sp | wild type | 0.688 | 0.491 |
| pKK104 | wild type | 3.2sp | 0.791 | 1.121 |
| pKK105 | wild type | 3.3sp | 1.335 | 1.115 |
| pKK107 | T-3.1 | wild type | 0.999 | 1.491 |
| pKK108 | T-3.5 | wild type | −0.090 | −0.204 |
| pKK109 | T-3.3 | wild type | 0.230 | 0.167 |
| pKK110 | T-5.1 | wild type | 1.492 | 2.556 |
| pKK111 | T-5.3 | wild type | 0.707 | 0.657 |
| pKK112 | T-AMY | wild type | 0.460 | 0.515 |

The results of phages displaying α3 domains with binding peptides inserted into more than one loop generated from pKK136, 138, and 139 along with controls are shown in Table 5. The ELISA assays of the integrin target-binding of M13 phages displaying α3 domains with binding peptide inserts grafted into more than one loop were performed as follows. After the respective integrins were adhered to the bottoms of the wells of the ELISA plate, the wells were washed and blocked. Each sample (100 μl) of phage preparation was added to wells containing αVβ3 or αVβ5, incubated and washed. The phages captured by the integrins were detected by HRP-conjugated antibody to the M13 phage coat developed with Ultra TMB-ELISA substrate and the optical densities read. The M13 phages titers ranged from $8\times10^{12}$ to $1.1\times10^{13}$/ml. The results of the phages displaying α3 domains with more than one peptide inserts generated from pKK136, 138, and 139, and controls displaying α3 domains with one insert generated from pKK93, 102, or 103 or no insert (pKK106) are shown. The amino acid sequences and SEQ ID NOs of their specific insert(s) are tabulated in Table 2. Those α3 domains with binding peptides inserted into more than 1 internal loop conveyed greater target binding of phages than do those with only a single internal binding peptide, confirming the avidity effect of more than 1 binding motif per molecule. Furthermore, the specificity of an α3 domain for its intended target, for example αVβ5, was again enhanced over the closely related target, αVβ3, when the α3 domain had more than one αVβ5-specific, internal binding peptide—the avidity effect.

TABLE 5

Integrin binding ELISA data from double inserts grafted in MICA α3-PIII bacteriophage display

| phage name | insert loop 1 | insert loop 3 | αvβ3 signal | αvβ5 signal |
|---|---|---|---|---|
| pKK106 | wild type | wild type | 0.000 | 0.000 |
| pKK93 | 3.2 | wild type | 0.616 | 0.774 |
| pKK102 | 5.1sp | wild type | 1.454 | 1.500 |
| pKK103 | 5.3sp | wild type | 0.587 | 0.814 |
| pKK136 | 5.1sp | 3.2sp | 2.462 | 4.280 |
| pKK138 | 5.1sp | 5.3sp | 0.886 | 2.748 |
| pKK139 | 5.1sp | 5.1sp.nh | 2.481 | 5.355 |

4. Soluble, Targeted MICA Acted as a Specific Adapter Molecule to Recruit NK Cells to Kill Target Cells The LIVE/DEAD® cell viability assays were carried out essentially as described by Chromy et al., 2000 and by the manufacturer's protocol (Invitrogen, Carlsbad, Calif.). Briefly, human target cells (MCF7 and HeLa) were seeded at a density of $1\times10^4$ cells/well in 96-well flat-bottomed culture plates and reached 80% confluency in 2 days. The culture supernatants of 293T cells transiently transfected with pKK131 were concentrated approximately 100-fold by Pierce 9K MWCO Concentrators and the MICA concentrations determined by the ELISA specific for MICA. To demonstrate the ability of soluble, targeted MICA molecules to recruit human NK cells to kill target cells, different concentrations of the concentrated soluble MICA protein were incubated for 16 hours in different wells containing the target cells. Unbound protein was then removed by washing the wells twice with phosphate buffered saline (PBS). The target cells exposed to the soluble MICA were then treated with calcein-AM (2 μM) for 30 minutes at 37° C. to achieve green fluorescence in all living cells. Following incubation, cells were again washed twice with PBS and then exposed to live NK-92MI cells in a 10:1 and 5:1 ratio to target cells. NK-92MI cells were incubated with target cells for four hours, and then unbound NK-92MI cells were removed and target cells washed twice with PBS. Next, ethidium homodimer was added (2 μM) for 30 min at 37° C. to determine the extent of NK cell killing. Cells were washed and analyzed on a fluorescent plate reader (SoftMaxPro). Live cells and dead cells were quantified using average of red (ethidium) and green (calcein-AM) fluorescence signals from wells in the absence of NK cells and at the 5:1 and 10:1 ratios and at 0, 64 pg and 128 pg of added soluble, targeted MICA.

The red fluorescent signals from (dead) MCF cells changed from 12.6±1.1 to 12.9±2.9 to 12.0±1.0 as NK cells were added at a ratio of 0 to 5:1 to 10:1 in the absence of targeted MICA. In the presence of 64 pg of targeted MICA, red fluorescent signals from (dead) MCF cells changed from 19.9±2.4 to 27.0±1.0 to 31.0±1.6 as NK cells were added at a ratio of 0 to 5:1 to 10:1. When targeted MICA was added at 128 pg, red fluorescent signals from (dead) MCF cells changed from 25.6±2.2 to 41.0±6.7 as NK cells were added at a ratio of 5:1 to 10:1. The corresponding fluorescent (green) signals from live cells in the same wells were 5621±372, 5535±205 and 5721±335 as NK cells were added at a ratio of 0 to 5:1 to 10:1 in the absence of targeted MICA. In the presence of 64 pg of targeted MICA, green fluorescent signals from live MCF cells changed from 5028±177 to 5181±102 to 3697±591 as NK cells were added at a ratio of 0 to 5:1 to 10:1. When targeted MICA was added at 128 pg, green fluorescent signals from live MCF cells changed from 3459±394 to 2191±331 as NK cells were added at a ratio of 5:1 to 10:1.

The fluorescent signals from HeLa cells, which do not express the targeted integrin, did not indicate increased killing by NK-92MI cells as increasing quantities of targeted MICA were added to the wells.

What is claimed is:

1. A non-natural, monomeric, soluble, mammalian MHC class I chain-related (MIC) molecule comprising an α1-α2 platform domain attached to a targeting motif,
wherein the α1-α2 platform domain is at least 80% identical to a native α1-α2 platform domain of a MIC protein, and wherein the α1-α2 platform domain binds an NKG2D receptor, and
wherein the targeting motif comprises a MIC α3 domain and one or more heterologous peptides, wherein the heterologous peptide or peptides are inserted into the MIC α3 domain within one or more sites in a solvent-exposed loop at a non-carboxy-terminal site, and wherein the heterologous peptide or peptides direct the binding of the targeting motif to one or more target molecules on one or more target cells, thereby delivering the attached α1-α2 platform domain to the target cell.

2. The molecule of claim 1 wherein the α1-α2 platform domain and the α3 domain are from a human MIC protein.

3. The molecule of claim 1 wherein the α1-α2 platform domain is at least 80% identical to a native α1-α2 platform domain of a human MICA or MICB protein, and wherein the α1-α2 platform domain binds an NKG2D receptor.

4. The molecule of claim 1, wherein the MIC molecule is glycosylated.

5. The molecule of claim 3, wherein the MICA or MICB protein is lacking its transmembrane domain.

6. The molecule of claim 3, wherein the MICA protein is selected from the group consisting of SEQ ID NOs:1-6, and 13.

7. The molecule of claim 3, wherein the MICB protein is selected from the group consisting of SEQ ID NOs:7-12.

8. The molecule of claim 1 wherein the α3 domain is a complete native α3 domain without a deletion.

9. The molecule of claim 1 wherein the α3 domain is a native α3 domain, wherein a portion of the domain has been deleted.

10. The molecule of claim 9, wherein the portion deleted is within 10 amino acid positions of the insertion site or sites of the heterologous peptide or peptides.

11. The molecule of claim 1, wherein the α3 domain comprises a deletion, insertion, amino acid substitution, mutation, or combination thereof at a site different from the insertion site.

12. The molecule of claim 1, wherein the solvent-exposed loops correspond to amino acid positions 190-199, 208-211, 221-228, 231-240, 250-258, and 264-266 of the α3 domain of a MIC protein selected from the group consisting of SEQ ID NOs:1-13.

13. The molecule of claim 10, wherein all or a portion of one or more of the solvent-exposed loops is deleted and replaced with the heterologous peptide or peptides.

14. The molecule of claim 13, wherein all of one or more of the solvent-exposed loops is deleted, and wherein further one, two, three, four, or five additional amino acids of the α3 domain adjacent to one or both sides of the deleted loop are deleted.

15. The molecule of claim 14, wherein a loop and two additional amino acids from both sides of the deleted loop are deleted, resulting in an overall deletion corresponding to amino acid positions 188-201, 219-230, or 248-260 of an α3 domain of a MIC protein selected from the group consisting of SEQ ID NOs:1-13.

16. The molecule of claim 12, wherein heterologous peptides that bind to the same target molecule are inserted into two or three of the solvent-exposed loops.

17. The molecule of claim 16, wherein the heterologous peptides comprise the same amino acid sequence.

18. The molecule of claim 13, wherein two or three of the loops are deleted and replaced with heterologous peptides that bind different target molecules.

19. The molecule of claim 16, wherein the target molecules are on the same cell or cell type.

20. The molecule of claim 16, wherein the target molecules are on different cells or cell types.

21. The molecule of claim 18, wherein the target molecules are on the same cell or cell type.

22. The molecule of claim 18, wherein the target molecules are on different cells or cell types.

23. The molecule of claim 1, wherein the target molecule is a cell-surface molecule.

24. The molecule of claim 1 wherein the target cell is malignant and the target molecule is an integrin, ErbB2, FGF1 Receptor, FGF2 Receptor, FGF3 Receptor, IGF1 Receptor, IGF2 Receptor, VEGF Receptor 1, VEGF Receptor 2, CD19, CD20, CD113, CD271, an oncogene-encoded protein product, or a fragment of any of the foregoing proteins.

25. The molecule of claim 1 wherein the target cell is infected by a virus and the target molecule on the target cell is a phosphotidylserine, or a phosphotidylserine with an accessory protein; or a surface glycoprotein encoded by a virus, an adenovirus, a human immunodeficiency virus, a herpetic virus, a pox virus, a flavivirus, a filovirus, a hepatitis virus, a papilloma virus, cytomegalovirus, vaccinia, rotavirus, influenza, a parvo virus, West Nile virus, rabies, polyoma, rubella, distemper virus, or Japanese encephalitis virus.

26. The molecule of claim 1 wherein the heterologous peptides are one or more complementarity determining regions of an antibody.

27. A composition comprising the non-natural, monomeric, MIC molecule of claim 1 and a carrier or excipient.

* * * * *

UNITED STATES PATENT AND TRADEMARK OFFICE
CERTIFICATE OF CORRECTION

PATENT NO. : 8,796,420 B2
APPLICATION NO. : 13/176601
DATED : August 5, 2014
INVENTOR(S) : David W. Martin, Jr. and Steven R. Williams Page 1 of 1

It is certified that error appears in the above-identified patent and that said Letters Patent is hereby corrected as shown below:

In the Specification

Column 20, line 61: the phrase "loop 2" should read "loop 3"

Columns 23 and 24 (Table 2): after the text ending "the corresponding SEQ ID NOs of the inserts." insert --("His10" disclosed as SEQ ID NO: 131).--

Columns 23 and 24 (Table 2): the sequence "ICQGEEQRFT" should read "CQGEEQRFT"

Signed and Sealed this
Second Day of June, 2015

Michelle K. Lee
*Director of the United States Patent and Trademark Office*

SEQUENCE LISTING

<160> NUMBER OF SEQ ID NOS: 131

<210> SEQ ID NO 1
<211> LENGTH: 274
<212> TYPE: PRT
<213> ORGANISM: Homo sapiens

<400> SEQUENCE: 1

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr Leu Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 2
<211> LENGTH: 274
<212> TYPE: PRT
<213> ORGANISM: Homo sapiens

<400> SEQUENCE: 2

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
         50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                    85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
            115                 120                 125

Met Pro Gln Ser Ser Arg Ala Gln Thr Leu Ala Met Asn Ile Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 3
<211> LENGTH: 274
<212> TYPE: PRT
<213> ORGANISM: Homo sapiens

<400> SEQUENCE: 3

Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

```
Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 4
<211> LENGTH: 274
<212> TYPE: PRT
<213> ORGANISM: Homo sapiens

<400> SEQUENCE: 4

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
                20                  25                  30

Phe Leu Arg Tyr Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Val Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240
```

```
Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 5
<211> LENGTH: 274
<212> TYPE: PRT
<213> ORGANISM: Homo sapiens

<400> SEQUENCE: 5

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 6
<211> LENGTH: 274
<212> TYPE: PRT
<213> ORGANISM: Homo sapiens

<400> SEQUENCE: 6

Glu Pro His Ser Leu Arg Tyr Asn Leu Thr Val Leu Ser Trp Asp Gly
```

```
  1               5                  10                 15
Ser Val Gln Ser Gly Phe Leu Ala Glu Val His Leu Asp Gly Gln Pro
             20                 25                 30

Phe Leu Arg Cys Asp Arg Gln Lys Cys Arg Ala Lys Pro Gln Gly Gln
             35                 40                 45

Trp Ala Glu Asp Val Leu Gly Asn Lys Thr Trp Asp Arg Glu Thr Arg
         50                 55                 60

Asp Leu Thr Gly Asn Gly Lys Asp Leu Arg Met Thr Leu Ala His Ile
65                  70                 75                 80

Lys Asp Gln Lys Glu Gly Leu His Ser Leu Gln Glu Ile Arg Val Cys
             85                 90                 95

Glu Ile His Glu Asp Asn Ser Thr Arg Ser Ser Gln His Phe Tyr Tyr
             100                105                110

Asp Gly Glu Leu Phe Leu Ser Gln Asn Leu Glu Thr Glu Glu Trp Thr
             115                120                125

Met Pro Gln Ser Ser Arg Ala Gln Thr Leu Ala Met Asn Val Arg Asn
         130                135                140

Phe Leu Lys Glu Asp Ala Met Lys Thr Lys Thr His Tyr His Ala Met
145                 150                155                160

His Ala Asp Cys Leu Gln Glu Leu Arg Arg Tyr Leu Lys Ser Gly Val
             165                170                175

Val Leu Arg Arg Thr Val Pro Pro Met Val Asn Val Thr Arg Ser Glu
             180                185                190

Ala Ser Glu Gly Asn Ile Thr Val Thr Cys Arg Ala Ser Gly Phe Tyr
             195                200                205

Pro Trp Asn Ile Thr Leu Ser Trp Arg Gln Asp Gly Val Ser Leu Ser
         210                215                220

His Asp Thr Gln Gln Trp Gly Asp Val Leu Pro Asp Gly Asn Gly Thr
225                 230                235                240

Tyr Gln Thr Trp Val Ala Thr Arg Ile Cys Gln Gly Glu Glu Gln Arg
             245                250                255

Phe Thr Cys Tyr Met Glu His Ser Gly Asn His Ser Thr His Pro Val
             260                265                270

Pro Ser

<210> SEQ ID NO 7
<211> LENGTH: 305
<212> TYPE: PRT
<213> ORGANISM: Homo sapiens

<400> SEQUENCE: 7

Pro His Ser Leu Arg Tyr Asn Leu Met Val Leu Ser Gln Asp Gly Ser
1               5                  10                 15

Val Gln Ser Gly Phe Leu Ala Glu Gly His Leu Asp Gly Gln Pro Phe
             20                 25                 30

Leu Arg Tyr Asp Arg Gln Lys Arg Arg Ala Lys Pro Gln Gly Gln Trp
             35                 40                 45

Ala Glu Asp Val Leu Gly Ala Lys Thr Trp Asp Thr Glu Thr Glu Asp
         50                 55                 60

Leu Thr Glu Asn Gly Gln Asp Leu Arg Arg Thr Leu Thr His Ile Lys
65                  70                 75                 80

Asp Gln Lys Gly Gly Leu His Ser Leu Gln Glu Ile Arg Val Cys Glu
             85                 90                 95

Ile His Glu Asp Ser Ser Thr Arg Gly Ser Arg His Phe Tyr Tyr Asp
```

```
            100                 105                 110
Gly Glu Leu Phe Leu Ser Gln Asn Leu Glu Thr Gln Glu Ser Thr Val
        115                 120                 125
Pro Gln Ser Ser Arg Ala Gln Thr Leu Ala Met Asn Val Thr Asn Phe
    130                 135                 140
Trp Lys Glu Asp Ala Met Lys Thr Lys Thr His Tyr Arg Ala Met Gln
145                 150                 155                 160
Ala Asp Cys Leu Gln Lys Leu Gln Leu Pro Pro Met Val Asn Val Ile
                165                 170                 175
Cys Ser Glu Val Ser Glu Gly Asn Ile Thr Val Thr Cys Arg Ala Ser
            180                 185                 190
Ser Phe Tyr Pro Arg Asn Ile Thr Leu Thr Trp Arg Gln Asp Gly Val
        195                 200                 205
Ser Leu Ser His Asn Thr Gln Gln Trp Gly Asp Val Leu Pro Asp Gly
    210                 215                 220
Asn Gly Thr Tyr Gln Thr Trp Val Ala Thr Arg Ile Arg Gln Gly Glu
225                 230                 235                 240
Glu Gln Arg Phe Thr Cys Tyr Met Glu His Ser Gly Asn His Gly Thr
                245                 250                 255
His Pro Val Pro Ser Gly Lys Ala Leu Val Leu Gln Ser Gln Arg Thr
            260                 265                 270
Asp Phe Pro Tyr Val Ser Ala Ala Met Pro Cys Phe Val Ile Ile Ile
        275                 280                 285
Ile Leu Cys Val Pro Cys Cys Lys Lys Lys Thr Ser Ala Ala Glu Gly
    290                 295                 300
Pro
305

<210> SEQ ID NO 8
<211> LENGTH: 317
<212> TYPE: PRT
<213> ORGANISM: Homo sapiens

<400> SEQUENCE: 8

Pro His Ser Leu Arg Tyr Asn Leu Met Val Leu Ser Gln Asp Gly Ser
1               5                   10                  15
Val Gln Ser Gly Phe Leu Ala Glu Gly His Leu Asp Gly Gln Pro Phe
            20                  25                  30
Leu Arg Tyr Asp Arg Gln Lys Arg Arg Ala Lys Pro Gln Gly Gln Trp
        35                  40                  45
Ala Glu Asp Val Leu Gly Ala Glu Thr Trp Asp Thr Glu Thr Glu Asp
    50                  55                  60
Leu Thr Glu Asn Gly Gln Asp Leu Arg Arg Thr Leu Thr His Ile Lys
65                  70                  75                  80
Asp Gln Lys Gly Gly Leu His Ser Leu Gln Glu Ile Arg Val Cys Glu
                85                  90                  95
Met His Glu Asp Ser Ser Thr Arg Gly Ser Arg His Phe Tyr Tyr Asn
            100                 105                 110
Gly Glu Leu Phe Leu Ser Gln Asn Leu Glu Thr Gln Glu Ser Thr Val
        115                 120                 125
Pro Gln Ser Ser Arg Ala Gln Thr Leu Ala Met Asn Val Thr Asn Phe
    130                 135                 140
Trp Lys Glu Asp Ala Met Lys Thr Lys Thr His Tyr Arg Ala Met Gln
145                 150                 155                 160
```

-continued

```
Ala Asp Cys Leu Gln Lys Leu Gln Arg Tyr Leu Lys Ser Gly Val Ala
            165                 170                 175
Ile Arg Arg Thr Val Pro Pro Met Val Asn Val Thr Cys Ser Glu Val
        180                 185                 190
Ser Glu Gly Asn Ile Thr Val Thr Cys Arg Ala Ser Ser Phe Tyr Pro
        195                 200                 205
Arg Asn Ile Thr Leu Thr Trp Arg Gln Asp Gly Val Ser Leu Ser His
        210                 215                 220
Asn Thr Gln Gln Trp Gly Asp Val Leu Pro Asp Gly Asn Gly Thr Tyr
225                 230                 235                 240
Gln Thr Trp Val Ala Thr Arg Ile Arg Gln Gly Glu Glu Gln Arg Phe
                245                 250                 255
Thr Cys Tyr Met Glu His Ser Gly Asn His Gly Thr His Pro Val Pro
            260                 265                 270
Ser Gly Lys Ala Leu Val Leu Gln Ser Gln Arg Thr Asp Phe Pro Tyr
        275                 280                 285
Val Ser Ala Ala Met Pro Cys Phe Val Ile Ile Ile Leu Cys Val
        290                 295                 300
Pro Cys Cys Lys Lys Lys Thr Ser Ala Ala Glu Gly Pro
305                 310                 315

<210> SEQ ID NO 9
<211> LENGTH: 317
<212> TYPE: PRT
<213> ORGANISM: Homo sapiens

<400> SEQUENCE: 9

Pro His Ser Leu Arg Tyr Asn Leu Met Val Leu Ser Gln Asp Gly Ser
1               5                   10                  15
Val Gln Ser Gly Phe Leu Ala Glu Gly His Leu Asp Gly Gln Pro Phe
            20                  25                  30
Leu Arg Tyr Asp Arg Gln Lys Arg Arg Ala Lys Pro Gln Gly Gln Trp
        35                  40                  45
Ala Glu Asp Val Leu Gly Ala Lys Thr Trp Asp Thr Glu Thr Glu Asp
    50                  55                  60
Leu Thr Glu Asn Gly Gln Asp Leu Arg Arg Thr Leu Thr His Ile Lys
65                  70                  75                  80
Asp Gln Lys Gly Gly Leu His Ser Leu Gln Glu Ile Arg Val Cys Glu
                85                  90                  95
Ile His Glu Asp Ser Ser Thr Arg Gly Ser Arg His Phe Tyr Tyr Asp
            100                 105                 110
Gly Glu Leu Phe Leu Ser Gln Asn Leu Glu Thr Gln Glu Ser Thr Val
        115                 120                 125
Pro Gln Ser Ser Arg Ala Gln Thr Leu Ala Met Asn Val Thr Asn Phe
    130                 135                 140
Trp Lys Glu Asp Ala Met Lys Thr Lys Thr His Tyr Arg Ala Met Gln
145                 150                 155                 160
Ala Asp Cys Leu Gln Lys Leu Gln Arg Tyr Leu Lys Ser Gly Val Ala
                165                 170                 175
Ile Arg Arg Thr Val Pro Pro Met Val Asn Val Ile Cys Ser Glu Val
            180                 185                 190
Ser Glu Gly Asn Ile Thr Val Thr Cys Arg Ala Ser Ser Phe Tyr Pro
        195                 200                 205
Arg Asn Ile Thr Leu Thr Trp Arg Gln Asp Gly Val Ser Leu Ser His
        210                 215                 220
```

```
Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
290                 295                 300

Pro Cys Cys Lys Lys Thr Ser Ala Ala Glu Gly Pro
305                 310                 315

<210> SEQ ID NO 10
<211> LENGTH: 317
<212> TYPE: PRT
<213> ORGANISM: Homo sapiens

<400> SEQUENCE: 10

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asn Val Leu Gly Ala Lys Thr Trp Asp Thr Glu Thr Glu Asp
50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
```

275                 280                 285
Val Ser Ala Ala Met Pro Cys Phe Val Ile Ile Ile Leu Cys Val
    290                 295                 300

Pro Cys Cys Lys Lys Lys Thr Ser Ala Ala Glu Gly Pro
305                 310                 315

<210> SEQ ID NO 11
<211> LENGTH: 317
<212> TYPE: PRT
<213> ORGANISM: Homo sapiens

<400> SEQUENCE: 11

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Lys Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
    290                 295                 300

Pro Cys Cys Lys Lys Lys Thr Ser Ala Ala Glu Gly Pro
305                 310                 315

<210> SEQ ID NO 12
<211> LENGTH: 317

<212> TYPE: PRT
<213> ORGANISM: Homo sapiens

<400> SEQUENCE: 12

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
290                 295                 300

Pro Cys Cys Lys Lys Thr Ser Ala Ala Glu Gly Pro
305                 310                 315

<210> SEQ ID NO 13
<211> LENGTH: 276
<212> TYPE: PRT
<213> ORGANISM: Homo sapiens

<400> SEQUENCE: 13

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
                35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Lys Glu Trp Thr
                115                 120                 125

Met Pro Gln Ser Ser Arg Ala Gln Thr Leu Ala Met Asn Val Arg Asn
                130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
                180                 185                 190

Ala Ser Glu Gly Asn Ile Thr Val Thr Cys Arg Ala Ser Gly Phe Tyr
                195                 200                 205

Pro Trp Asn Ile Thr Leu Ser Trp Arg Gln Asp Gly Val Ser Leu Ser
                210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser Gly Lys
        275

<210> SEQ ID NO 14
<211> LENGTH: 937
<212> TYPE: DNA
<213> ORGANISM: Homo sapiens

<400> SEQUENCE: 14
gctagcgctg agagggtggc gacgtcgggg ccatggggct gggcccggtc ttcctgcttc    60
tggctggcat cttcccttttt gcacctccgg gagctgctgc tgagccccac agtcttcgtt   120
ataacctcac ggtgctgtcc tgggatggat ctgtgcagtc agggtttctc actgaggtac   180
atctggatgg tcagcccttc ctgcgctgtg acaggcagaa atgcagggca aagccccagg   240
gacagtgggc agaagatgtc ctgggaaata gacatgggca gagagacc agggacttga    300 cagggaacgg aaaggacctc aggatgaccc tggctcatat caaggaccag aaagaaggct   360
tgcattccct ccaggagatt agggtctgtg agatccatga agacaacagc accaggagct   420
cccagcattt ctactacgat ggggagctct tcctctccca aacctggaga ctaaggaatg   480
gacaatgccc cagtcctcca gagctcagac cttggccatg aacgtcagga atttcttgaa   540
ggaagatgcc atgaagacca agacacacta tcacgctatg catgcagact gcctgcagga   600
actacgcgca tatctaaaat ccggcgtagt cctgaggaga acagtgcccc ccatggtgaa   660
tgtcacccgc agcgaggcct cagagggcaa cattaccgtg acatgcaggg cttctggctt   720

```
ctatccctgg aatatcacac tgagctggcg tcaggatggg gtatctttga gccacgacac      780
ccagcagtgg ggggatgtcc tgcctgatgg gaatggaacc taccagacct gggtggccac      840
caggatttgc caaggagagg agcagaggtt cacctgctac atggaacaca gcgggaatca      900
cagcactcac cctgtgccct ctgggaaata aagctt                               937

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tatgaaatac ctgctgccga ccgctgctgc tggtctgctg ctcctcgctg cccagcc         57

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
catgggctgg gcagcgagga gcagcagacc agcagcagcg gtcggcagca ggtatttca       59

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
catgcatcat caccatcacc acctcgagga attcaagctt ggatccgc                   48

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcagcggatc caagcttgaa ttcctcgagg tggtgatggt gatgatg                    47

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 tttttttgcta gcgctgagag ggtggcgacg tc                                   32

<210> SEQ ID NO 20
<211> LENGTH: 36
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 20
ctttccaagc ttttatttcc cagagggcac agggtg                                 36

<210> SEQ ID NO 21
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tccctcctcg aggaaaactt gtactttcaa ggcgagcccc acagtcttcg ttataacc         58

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22 cccccggat ccatgattac tcatggttgt tatacccg                                38

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23 cccccaagc ttattctaca caaaccgcat agac                                    34

<210> SEQ ID NO 24
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 tttttttctcg aggtggtgat ggtgatgatg tcggccttca ataccgccgc tggccttggt      60
ttgatc                                                                  66

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 ccccccata tgattactca tggttgttat acccgg                                  36

<210> SEQ ID NO 26
<211> LENGTH: 65
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 26
aaaaaactcg aggaaaactt gtactttcaa ggcacagtgc cacccatggt gaatgtcacc        60
cgcag                                                                   65

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atatataagc ttttatttcc cagagggcac                                        30

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 tttttcgtc tctcatgatt actcatggt                                          29

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atatacatac agtcgaccag gttgggggcg gtattgaagg ccgacatc                    48

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30 tttttttgcta gcgctgagag ggtggcgacg tc                                    32

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctttccaagc ttttatttcc cagagggcac aggtg                                  36

<210> SEQ ID NO 32
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aatcacagca ctcaccctgt gccc                                            24

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcccttcgtc tctggtcgga tacgctgtcg aacttttcga tc                        42

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaatcctggt ggccacccag gtctgg                                          26

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagacgacaa acgtctcttg ctacatggaa cacagcggga atc                       43

<210> SEQ ID NO 36
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gattagtggt ggcagtggcg gcggtagtca tcatcaccac catcaccacc atcaccacag     60
cggcggcagc ggtggcggt                                                  79

<210> SEQ ID NO 37
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agcaaccgcc accgctgccg ccgctgtggt gatggtggtg atggtggtga tgatgactac     60
cgccgccact gccaccact                                                  79
```

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Gly Gly Ser Gly Gly Gly Ser His His His His His His His
1               5                   10                  15

His His Ser Gly Gly Ser Gly Gly Gly
            20                  25

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agtcagggtt tctcactgag gtacatctgg                                      30

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcacagatcc atcccaggac agcaccgtga g                                    31

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
catcatcatg agccccacag tcttcgttat aacc                                 34

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtggtggtga gcagcagctc ccggaggtgc aaaaggg                              37

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Arg Gly Asp His Pro Arg Thr Gln
1               5

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cacctctcgg ggcgatcacc ctcgcaccca g                                    31

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcacctgggt gcgagggtga tcgccccgag a                                    31

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Thr Ser Arg Gly Asp His Pro Arg Thr Gln
1               5                   10

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caccaggaca tctcggggcg atcaccctcg cacccag                              37

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcacctgggt gcgagggtga tcgccccgag atgtcct                              37

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Arg Val Pro Arg Gly Asp Ser Asp Leu Thr
1               5                   10

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caccagggtg cctcggggcg atagcgatct gacc                              34

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tcacggtcag atcgctatcg ccccgaggca ccct                              34

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ala Arg Gly Asp Ser Asp His Arg
1               5                   10

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caccaggagc gcccggggcg atagcgatca ccgg                              34

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcacccggtg atcgctatcg ccccgggcgc tcct                              34

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 55

Val Thr Arg Gly Asp Thr Phe Thr Gln Ser
1               5                   10

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
caccgtgaca cggggcgata ctttcacaca gtcc                               34

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tcacggactg tgtgaaagta tcgccccgtg tcac                               34

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Gly Asp Thr Phe Thr Gln Ser
1               5

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cacccggggc gatactttca cacagtcc                                      28

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tcacggactg tgtgaaagta tcgccccg                                      28

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

His Leu Ala Arg Gly Asp Asp Leu Thr Tyr
1               5                   10

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cacccacctg gcacggggcg atgacctgac atac                                34

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tcacgtatgt caggtcatcg ccccgtgcca ggtg                                34

<210> SEQ ID NO 64
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gly Gly Ser Gly Gly Gly Ser Thr Ser Arg Gly Asp His Pro Arg
1               5                   10                  15

Thr Gln Ser Gly Gly Ser Gly Gly Gly
            20                  25

<210> SEQ ID NO 65
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
caccagtggt ggcagtggcg gcggtagtac atctcggggc gatcaccctc gcacccagag    60
cggcggcagc ggtggcggt                                                 79

<210> SEQ ID NO 66
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcacaccgcc accgctgccg ccgctctggg tgcgagggtg atcgccccga gatgtactac    60
cgccgccact gccaccact                                                 79

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gly Gly Ser Gly Gly Gly Ser Arg Val Pro Arg Gly Asp Ser Asp
1               5                   10                  15

Leu Thr Ser Gly Gly Ser Gly Gly Gly
            20                  25

<210> SEQ ID NO 68
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
caccagtggt ggcagtggcg gcggtagtag ggtgcctcgg ggcgatagcg atctgaccag    60
cggcggcagc ggtggcggt                                                79

<210> SEQ ID NO 69
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tcacaccgcc accgctgccg ccgctggtca gatcgctatc gccccgaggc accctactac    60
cgccgccact gccaccact                                                79

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Gly Gly Ser Gly Gly Gly Ser Val Thr Arg Gly Asp Thr Phe Thr
1               5                   10                  15

Gln Ser Ser Gly Gly Ser Gly Gly Gly
            20                  25

<210> SEQ ID NO 71
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caccagtggt ggcagtggcg gcggtagtgt gacacggggc gatactttca cacagtccag    60
cggcggcagc ggtggcggt                                                79

<210> SEQ ID NO 72
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tcacaccgcc accgctgccg ccgctggact gtgtgaaagt atcgccccgt gtcacactac    60
cgccgccact gccaccact                                                 79

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gly Gly Ser Gly Gly Gly Ser His Leu Ala Arg Gly Asp Asp Leu
1               5                   10                  15

Thr Tyr Ser Gly Gly Ser Gly Gly Gly
            20                  25

<210> SEQ ID NO 74
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
caccagtggt ggcagtggcg gcggtagtca cctggcacgg ggcgatgacc tgacatacag    60
cggcggcagc ggtggcggt                                                 79

<210> SEQ ID NO 75
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcacaccgcc accgctgccg ccgctgtatg tcaggtcatc gccccgtgcc aggtgactac    60
cgccgccact gccaccact                                                 79

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Gly Gly Ser Gly Gly Gly Ser Thr Ser Arg Gly Asp His Pro Arg
1               5                   10                  15

Thr Gln Ser Gly Gly Ser Gly Gly Gly
            20                  25

<210> SEQ ID NO 77
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gattagtggt ggcagtggcg gcggtagtac atctcggggc gatcaccctc gcacccagag    60
cggcggcagc ggtggcggt                                                 79

<210> SEQ ID NO 78
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agcaaccgcc accgctgccg ccgctctggg tgcgagggtg atcgccccga gatgtactac    60
cgccgccact gccaccact                                                 79

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Gly Gly Ser Gly Gly Gly Ser Arg Val Pro Arg Gly Asp Ser Asp
1               5                   10                  15

Leu Thr Ser Gly Gly Ser Gly Gly Gly
            20                  25

<210> SEQ ID NO 80
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gattagtggt ggcagtggcg gcggtagtag ggtgcctcgg ggcgatagcg atctgaccag    60
cggcggcagc ggtggcggt                                                 79

<210> SEQ ID NO 81
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
agcaaccgcc accgctgccg ccgctggtca gatcgctatc gccccgaggc accctactac    60
cgccgccact gccaccact                                                 79

```
<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Gly Gly Ser Gly Gly Gly Ser Val Thr Arg Gly Asp Thr Phe Thr
1               5                   10                  15

Gln Ser Ser Gly Gly Ser Gly Gly Gly
            20                  25

<210> SEQ ID NO 83
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gattagtggt ggcagtggcg gcggtagtgt gacacggggc gatactttca cacagtccag      60
cggcggcagc ggtggcggt                                                  79

<210> SEQ ID NO 84
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agcaaccgcc accgctgccg ccgctggact gtgtgaaagt atcgccccgt gtcacactac      60
cgccgccact gccaccact                                                  79

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Gly Gly Ser Gly Gly Gly Ser His Leu Ala Arg Gly Asp Asp Leu
1               5                   10                  15

Thr Tyr Ser Gly Gly Ser Gly Gly Gly
            20                  25

<210> SEQ ID NO 86
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gattagtggt ggcagtggcg gcggtagtca cctggcacgg ggcgatgacc tgacatacag      60
cggcggcagc ggtggcggt                                                  79
```

```
<210> SEQ ID NO 87
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agcaaccgcc accgctgccg ccgctgtatg tcaggtcatc gccccgtgcc aggtgactac      60
cgccgccact gccaccact                                                  79

<210> SEQ ID NO 88
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ttaattaacg tctcatgcag ggcttctggc ttctatccct g                         41

<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acgtctcgat tcaccatggg gggcactgtt ctcctc                               36

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Ser Arg Gly Asp His Pro Arg Thr Gln
1               5                   10

<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaatacaagc cgaggtgacc acccacgtac acaa                                 34

<210> SEQ ID NO 92
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tgcattgtgt acgtgggtgg tcacctcggc ttgt                                 34
```

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Arg Gly Asp Ser Leu Ile Met His
1               5                   10

<210> SEQ ID NO 94
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaatggttca cgaggtgact cattgattat gcac                                34

<210> SEQ ID NO 95
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgcagtgcat aatcaatgag tcacctcgtg aacc                                34

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Val Pro Arg Gly Asp Ser Asp Leu Thr
1               5                   10

<210> SEQ ID NO 97
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gaatcgagta ccacgaggtg actcagattt gact                                34

<210> SEQ ID NO 98
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tgcaagtcaa atctgagtca cctcgtggta ctcg                                    34

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Val Thr Arg Gly Asp Thr Phe Thr Gln Ser
1               5                   10

<210> SEQ ID NO 100
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gaatgtaaca cgaggtgaca cattcactca gagc                                    34

<210> SEQ ID NO 101
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgcagctctg agtgaatgtg tcacctcgtg ttac                                    34

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

His Leu Ala Arg Gly Asp Asp Leu Thr Tyr
1               5                   10

<210> SEQ ID NO 103
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gaatcacttg gcacgaggtg acgatctcac atac                                    34

<210> SEQ ID NO 104
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgcagtatgt gagatcgtca cctcgtgcca agtg              34

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Gln Ser Trp Arg Tyr Ser Gln
1               5

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gaattaccag tcttggcgtt actctcag              28

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tgcactgaga gtaacgccaa gactggta              28

<210> SEQ ID NO 108
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gaatcctggt ggccacccag gtctgg              26

<210> SEQ ID NO 109
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gagacgacaa acgtctcttg ctacatggaa cacagcggga atc              43

<210> SEQ ID NO 110
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
gatttccgga ggttctggag gtggctcggt aacccgagga gacacctta cccaaagttc    60 aggaggttca ggaggtgga                                                 79
```

<210> SEQ ID NO 111
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111

```
agcatccacc tcctgaacct cctgaacttt gggtaaaggt gtctcctcgg gttaccgagc    60
cacctccaga acctccgga                                                 79
```

<210> SEQ ID NO 112
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112

```
cctccgaatt cggatcctag gcggctcctt atttgtttgt gaatatcaag gcc           53
```

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113

```
ccctccaagc ttaagactcc ttattacgca gtatg                               35
```

<210> SEQ ID NO 114
<211> LENGTH: 299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
gaattcatga aaaattatt attcgcaatt cctttagtgg tacctttcta ttctcactcg    60
gactacaagg atgacgacga taagcaattg aaccagcgc catcttgcgt taccctgtac    120
cagtcttggc gttactctca ggctgacaac ggttgcgcag aaacggttac cgtaaaagtg   180
gtatacgaag acgacaccga gggcctgtgc tacgcagttg ccccgggtca gatcaccact   240
gttggtgacg gctacatcgg ctctcacggt cacgctcggt atctggctcg ttgcctagg    299
```

<210> SEQ ID NO 115
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
gaattcatga aaaattatt attcgcaatt cctttagtgg tacctttcta ttctcactcg    60
```

```
gactacaagg atgacgacga taagcaattg gaaccagcgc catcttgcgt taccctgaca    120
tcacgaggcg accacccacg cacccaggct gacaacggtt gcgcagaaac ggttaccgta    180
aaagtggtat acgaagacga caccgagggc ctgtgctacg cagttgcccc gggtcagatc    240
accactgttg gtgacggcta catcggctct cacggtcacg ctcggtatct ggctcgttgc    300
ctagg                                                                305
```

<210> SEQ ID NO 116
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
gaattcatga aaaattatt attcgcaatt cctttagtgg taccttcta ttctcactcg     60 gactacaagg atgacgacga taagcaattg gaaccagcgc catcttgcgt taccctgggc    120
tcacgaggcg actccctcat catgcacgct gacaacggtt gcgcagaaac ggttaccgta    180
aaagtggtat acgaagacga caccgagggc ctgtgctacg cagttgcccc gggtcagatc    240
accactgttg gtgacggcta catcggctct cacggtcacg ctcggtatct ggctcgttgc    300
ctagg                                                                305
```

<210> SEQ ID NO 117
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
gaattcatga aaaattatt attcgcaatt cctttagtgg taccttcta ttctcactcg     60 gactacaagg atgacgacga taagcaattg gaaccagcgc catcttgcgt taccctggta    120
acacgaggcg acaccttcac gcagtccgct gacaacggtt gcgcagaaac ggttaccgta    180
aaagtggtat acgaagacga caccgagggc ctgtgctacg cagttgcccc gggtcagatc    240
accactgttg gtgacggcta catcggctct cacggtcacg ctcggtatct ggctcgttgc    300
ctagg                                                                305
```

<210> SEQ ID NO 118
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
gaattcatga aaaattatt attcgcaatt cctttagtgg taccttcta ttctcactcg     60 gactacaagg atgacgacga taagcaattg gaaccagcgc catcttgcgt taccctgcac    120
ctggcacgag gcgacgatct tacctacgct gacaacggtt gcgcagaaac ggttaccgta    180
aaagtggtat acgaagacga caccgagggc ctgtgctacg cagttgcccc gggtcagatc    240
accactgttg gtgacggcta catcggctct cacggtcacg ctcggtatct ggctcgttgc    300
ctagg                                                                305
```

<210> SEQ ID NO 119
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
gaattcatga aaaaattatt attcgcaatt cctttagtgg tacctttcta ttctcactcg    60
gactacaagg atgacgacga taagcaattg gaaccagcgc catcttgcgt taccctgcac   120
caccaccatc accatcatca ttcacaagct gacaacggtt gcgcagaaac ggttaccgta   180
aaagtggtat acgaagacga caccgagggc ctgtgctacg cagttgcccc gggtcagatc   240
accactgttg gtgacggcta catcggctct cacggtcacg ctcggtatct ggctcgttgc   300
ctagg                                                               305

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cttcccgaat tcatgacagt gccacccatg gtgaatgtca c                        41

<210> SEQ ID NO 121
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tttcttcgtc tcactagttt cccagagggc acagggtgag tg                       42

<210> SEQ ID NO 122
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cttcccgaat tcatgacagt gcccccatg gtgaatacaa g                         41

<210> SEQ ID NO 123
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cttcccgaat tcatgacagt gcccccatg gtgaatggtt ca                        42

<210> SEQ ID NO 124
<211> LENGTH: 42

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cttcccgaat tcatgacagt gcccccatg gtgaatcgag ta                        42

<210> SEQ ID NO 125
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cttcccgaat tcatgacagt gcccccatg gtgaatgtaa ca                        42

<210> SEQ ID NO 126
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cttcccgaat tcatgacagt gcccccatg gtgaatcact tg                        42

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 127

His His His His His His
1               5

<210> SEQ ID NO 128
<211> LENGTH: 7
<212> TYPE: PRT
<213> ORGANISM: Unknown
<220> FEATURE:
<223> OTHER INFORMATION: Description of Unknown: Tev protease cleavage
      site peptide

<400> SEQUENCE: 128

Glu Asn Leu Tyr Phe Gln Gly
1               5

<210> SEQ ID NO 129
<211> LENGTH: 4
<212> TYPE: PRT
<213> ORGANISM: Unknown
<220> FEATURE:
<223> OTHER INFORMATION: Description of Unknown: Factor Xa cleavage
      site peptide

<400> SEQUENCE: 129

Ile Glu Gly Arg
1
```

```
<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 130

His His His His His His His His
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 131

His His His His His His His His His His
1               5                   10
```